US011884685B2

(12) United States Patent
King et al.

(10) Patent No.: US 11,884,685 B2
(45) Date of Patent: Jan. 30, 2024

(54) RHENIUM COMPLEXES AND METHODS OF USE FOR TREATING CANCER

(71) Applicant: CORNELL UNIVERSITY, Ithaca, NY (US)

(72) Inventors: Arthur Paden King, Rockville, MD (US); Sierra C. Marker, Rockville, MD (US); Robert Swanda, Windsor, NY (US); Shu-Bing Qian, Ithaca, NY (US); Justin J. Wilson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/267,687

(22) PCT Filed: Aug. 16, 2019

(86) PCT No.: PCT/US2019/046732
§ 371 (c)(1),
(2) Date: Feb. 10, 2021

(87) PCT Pub. No.: WO2020/037166
PCT Pub. Date: Feb. 20, 2020

(65) Prior Publication Data
US 2021/0317151 A1 Oct. 14, 2021

Related U.S. Application Data

(60) Provisional application No. 62/765,059, filed on Aug. 16, 2018.

(51) Int. Cl.
*C07F 13/00* (2006.01)
*A61P 35/00* (2006.01)

(52) U.S. Cl.
CPC ............. *C07F 13/00* (2013.01); *A61P 35/00* (2018.01)

(58) Field of Classification Search
None
See application file for complete search history.

(56) References Cited

FOREIGN PATENT DOCUMENTS

JP 2002173674 A 6/2002
WO 2017/223428 A1 12/2017

OTHER PUBLICATIONS

Villegas ("A spectroscopic and computational study on the effects of methyl and phenyl substituted phenanthroline ligands on the electronic structure of Re(I) tricarbonyl complexes containing 2,3-dimethylphenylisocyanide" Dalton Trans, 2005, p. 1042-1051). (Year: 2005).*

(Continued)

*Primary Examiner* — Amy C Bonaparte
(74) *Attorney, Agent, or Firm* — FOLEY & LARDNER LLP

(57) ABSTRACT

A composition comprising the following structure: (1) wherein Re represents a rhenium ion having a +1 charge; (I) represents an uncharged bidentate ligand containing at least one ring containing a ring nitrogen atom bound to the rhenium (Re), and the bidentate ligand containing another nitrogen atom, either in a ring or not in a ring, bound to the rhenium (Re); and $L^1$, $L^2$, $L^3$, and $L^4$ are neutral ligands with at least one neutral ligand being an isonitrile ligand of the formula —CN—R, wherein R is an aliphatic or aromatic hydrocarbon group containing 1-20 carbon atoms; and $X^-$ represents a non-coordinating monovalent anion; wherein the bidentate ligand and R are optionally substituted by one or more groups selected from (i)-(xi) as further discussed above. Methods for treating a condition that benefits from (Continued)

ER stress induction, such as cancer, by administering the above rhenium complex are also disclosed.

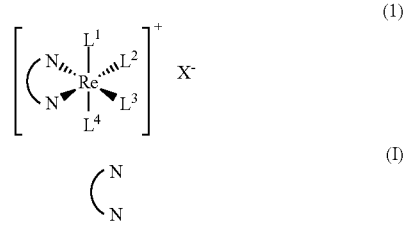

(I)

$$\begin{bmatrix} & L^1 & \\ N_{\textit{\tiny{I\!I\!I}}} & | & \textit{\tiny{\!\!\!\!\!}}L^2 \\ & Re & \\ N & | & L^3 \\ & L^4 & \end{bmatrix}^+ X^-$$

(I)

$\underset{N}{\overset{N}{\bigg(}}$

22 Claims, 4 Drawing Sheets

(56) References Cited

OTHER PUBLICATIONS

Sacksteder ("Long-Lived, Highly Luminescent Rhenium(I) Complexes as Molecular Probes: Intra- and Intermolecular Excited-State Interactions" J. Am. Chem. Soc. 1993, 115, p. 8230-8238) (Year: 1993).*

Ethanol (downloaded from https://www.ema.europa.eu/en/documents/scientific-guideline/information-package-leaflet-regarding-ethanol-used-excipient-medicinal-products-human-use_en.pdf on Mar. 21, 2023). (Year: 2023).*

Ko ("Synthesis, Characterization, and Photophysical and Emission Solvatochromic Study of Rhenium(I) Tetra(isocyano) Diimine Complexes" Organometallics, 2011(30), p. 2701-2711) (Year: 2011).*

Darensbourg, D.J., et al., "A New Water-Soluble Phosphine Derived from 1,3,5-Triaza-7-phosphaadamantane(PTA),3,7-Diacetyl-1,3,7-triaza-5-phosphabicyclo[3.3.1]nonane.Structural, Bonding, and Solubility Properties", Organometallics, 2004, pp. 1747-1754, vol. 23, No. 8.

International Search Report and Written Opinion dated Dec. 18, 2019 issued in PCT/US2019/046732, 10 pages.

King, A.P., et al., "A Rhenium Isonitrile Complex Induces Unfolded Protein Response-Mediated Apoptosis in Cancer Cells", Chem. Eur. J., 2019, pp. 9206-9210, 25.

Knopf, K.M., et al., "In Vitro Anticancer Activity and in Vivo Biodistribution of Rhenium(I) Tricarbonyl Aqua Complexes", Journal of the American Chemical Society, 13 pages.

Kurz, P., et al., "Ligand Variations in [ReX(diimine)(CO)3] Complexes: Effects on Photocatalytic CO2 Reduction", Eur. J. Inorg. Chem. 2006, pp. 2966-2974.

Marker, S.C., et al., "Photoactivated in Vitro Anticancer Activity of Rhenium(!) Tricarbonyl Complexes Bearing Water-Soluble Phosphines", Inorg. Chem. 2018, Published Jan. 11, 2018, pp. 1311-1331, 57.

Ng, C., et al., "A New Class of Isocyanide-Containing Rhenium(!) Bipyridyl Luminophore with Readily Tunable and Highly Environmentally Sensitive Excited-State Properties", Inorg. Chem. 2008, Jul. 29, 2018, pp. 7447-7449, 47, 17, abstract only.

Pierri, A.E., et al., "A Luminescent and Biocompatible PhotoCORM", J. Am. Chem. Soc. 2012, Published Oct. 18, 2012, pp. 18197-18200, 134.

Smieja, J.M., et al., "Re(bipy-tBu)(CO) Dioxide: IR-Spectroelectrochemical and Mechanistic Studies", Inorg. Chem. 2010, Published on Web Sep. 16, 2010, pp. 9283-9289, 49.

Wilson, J.J., "Rhenium as an Alternative to Platinum for the Treatment of Cancer", 256th ACS National Meeting Boston, MA, Aug. 19, 2018, 33 pages.

Yuan, Y., et al., "Visible-Light-Induced Radical Cascade Cyclization: Synthesis of the ABCD Ring Cores of Camptothecins", J. Org. Chem. 2018, Published Feb. 7, 2018, pp. 2840-2846, 83.

* cited by examiner

RHENIUM COMPLEXES AND METHODS OF USE FOR TREATING CANCER

CROSS REFERENCE TO RELATED APPLICATION

The present application claims benefit of U.S. Provisional Application No. 62/765,059, filed on Aug. 16, 2018, all of the contents of which are incorporated herein by reference.

STATEMENT REGARDING FEDERALLY SPONSORED RESEARCH OR DEVELOPMENT

This invention was made with government support under Grant No. W81XWH-17-1-0097, awarded by the Department of Defense Ovarian Cancer Research Program. The government has certain rights in the invention.

FIELD OF THE INVENTION

The invention relates generally to rhenium complexes and methods for treating conditions that could benefit from ER stress induction, particularly cancer, by administering the rhenium complex to a subject having such a condition. The invention is more particularly directed to rhenium(I) complexes coordinated to neutral ligands and their use in treating various cancers, particularly platinum-resistant cancers, or in particular, ovarian cancer.

BACKGROUND

Many cancers, such as ovarian cancer, are currently being treated with platinum-based chemotherapeutic agents, such as cisplatin or carboplatin. Although the platinum-based agents have significantly contributed to the treatment of cancer, they have several limitations, including susceptibility to relapse and platinum resistance. Moreover, the broad cytotoxicity of the platinum agents often results in substantial side effects.

The chemotherapeutic drug, cisplatin, is used in over 50% of all cases of cancer. This cytotoxic agent is used as the first-line treatment for several cancer types, including testicular and ovarian cancers. Despite its clinical success, it is limited by toxic side effects, and a decreased efficacy due to both inherent and acquired resistance of tumor cells to this drug. The design of improved agents, capable of circumventing cisplatin-resistance, is needed.

Of the cancers, there is a particular need for improved treatment of ovarian cancer. Ovarian cancer is the fifth most common cancer-related death in women (Siegel, R., et al. Cancer Statistics, 2012, CA. Cancer J. Clin., 2012, 62, 10-29). Treatment is manageable at early stages of the disease using the platinum-based chemotherapeutic agents, cisplatin and carboplatin (Raja, F. A., et al. Optimal First-Line Treatment in Ovarian Cancer, Ann. Oncol., 2012, 23, x118-x127). However, relapse is common and has a substantially poorer prognosis, with median survival times between 12-24 months (Armstrong, D. K., Relapsed Ovarian Cancer: Challenges and Management Strategies for a Chronic Disease, Oncologist, 2002, 7, 20-28).

Platinum-based drugs have several limitations for treating relapsed ovarian cancer. For example, the relapsed tumors are frequently platinum-resistant, rendering cisplatin and carboplatin treatments ineffective (Agarwal, R., et al. Ovarian Cancer: Strategies for Overcoming Resistance to Chemotherapy, Nat. Rev. Cancer, 2003, 3, 502-516) and the broad cytotoxicity of the platinum agent can give rise to significant side effects (Florea, A. -M., et al. Cisplatin as an Anti-Tumor Drug: Cellular Mechanisms of Activity, Drug Resistance and Induced Side Effects, Cancers, 2011, 3, 1351-1371). The platinum-based drugs also typically have substantial formulation challenges, such as poor water solubility and low stability in aqueous solution. Furthermore, direct in vivo or in vitro imaging of the distribution of the platinum drugs is generally not possible using conventional methods. Drugs or drug candidates that bear such imaging modalities (i.e., theragnostic agents) can achieve the real-time evaluation of drug response and distribution, facilitating the evaluation of patient dosage and response. New chemotherapeutic agents that overcome the treatment limitations of the platinum drugs and simultaneously serve as theragnostic agents would greatly benefit the treatment of various cancers, particularly ovarian cancer.

SUMMARY OF THE DISCLOSURE

In one aspect, the present disclosure is directed to rhenium (I) complexes (i.e., "$Re^{+1}$ complexes") in which the rhenium (I) is bonded to all neutral (uncharged) ligands, including at least one isonitrile ligand and a bidentate ligand bound to the rhenium by two nitrogen atoms. The rhenium(I) complexes are useful in treating conditions in which inducing ER (endoplasmic reticulum) stress is beneficial. In particular embodiments, the rhenium(I) compounds are useful in treating cancer by inducing ER stress. The rhenium(I) compounds described herein are advantageously stable, substantially water soluble, and substantially cytotoxic to cancer cells. The bidentate ligand is typically heteroaromatic and contains at least one ring nitrogen atom that coordinates to the rhenium(I), e.g., a ligand having a bipyridyl, phenanthryl, or naphthyridyl core structure. In the complex, the rhenium(I) is charge balanced by a non-coordinating monovalent anion, such as $SO_3CF_3^-$, $PF_6^-$, tosylate, $SbF_6^-$, borate anions, $AsF_6^-$, $ClO_4^-$, and carborane anions. As halide anions (e.g., $Cl^-$) are not neutral ligands and may also coordinate to the rhenium(I), they are excluded as a neutral ligand and may also be excluded as an anion.

More specifically, the rhenium complexes have the following general structure:

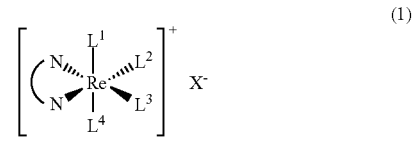

In the above Formula (1), Re represents a rhenium ion having a +1 charge;

represents an uncharged bidentate ligand containing at least one ring containing a ring nitrogen atom bound to the rhenium (Re), and the bidentate ligand containing another nitrogen atom, either in a ring or not in a ring, bound to the rhenium (Re); and $L^1$, $L^2$, $L^3$, and $L^4$ are neutral ligands independently selected from CO, neutral phosphine molecules, solvent molecules, and isonitrile ligands of the formula —CN—R, wherein R is an aliphatic or aromatic hydrocarbon group containing 1-20 carbon atoms, and wherein at least one of L¹, L², L³, and L⁴ is an isonitrile ligand; and X⁻ represents a non-coordinating monovalent anion; and
wherein

is optionally substituted on at least one of its rings with at least one of the following substituents: (i) hydrocarbon group (R') containing 1-6 carbon atoms; ii) —OR$^a$ groups; (iii) —C(O)OR$^a$ groups; (iv) —OC(O)R$^a$ groups; (v) —C(O)R$^a$ groups; (vi) —NR$^a{}_2$ groups; (vii) —C(O)NR$^a{}_2$ groups; (viii) —NR$^a$C(O)R$^a$ groups; (ix) halogen atoms, (x) —CN groups, and (xi) nitro (NO$_2$) groups, wherein said hydrocarbon groups R and R' optionally include one or more heteroatoms selected from oxygen, nitrogen, sulfur, and halogen atoms, and R is optionally substituted with one or more of the substituents (i)-(xi) recited above, and R$^a$ is independently selected from hydrogen atoms and hydrocarbon groups R'.

In another aspect, the present disclosure is directed to a method for treating conditions in which inducing ER stress is beneficial. In particular embodiments, the method is directed to treating cancer by inducing ER stress. In particular embodiments, the method is directed to treating cancer in a subject by administering to the subject a pharmaceutically effective amount of a rhenium complex according to Formula (1), as described above. Typically, the rhenium complex is administered as a solution or suspension that contains the rhenium complex dispersed in a pharmaceutically acceptable carrier. In some embodiments, the cancer is a platinum-resistant cancer. The cancer may be selected from, for example, ovarian cancer, cervical cancer, testicular cancer, prostate cancer, breast cancer, lung cancer, mesothelioma, squamous cell cancer, bladder cancer, lymphatic cancer, esophageal cancer, stomach cancer, gastrointestinal cancer, head-and-neck cancer, skin cancer, and pancreatic cancer.

The above-described rhenium complexes and their use for the treatment of cancer by inducing ER stress represents an advance in the field of cancer treatment by providing an efficacious alternative to platinum-based agents. The alternatives described herein are based on rhenium(I) complexes instead of platinum complexes. The complexes described herein have surprisingly been found herein to have at least the potency (i.e., level of cytotoxicity) or even greater potency than cisplatin and/or other platinum-based drugs of the art in the treatment of cancer. In addition, the complexes described herein have surprisingly been found herein to exhibit effective anti-cancer activity in cisplatin-resistant cell lines. Moreover, the complexes described herein have been surprisingly found herein to possess a significantly lower or substantially no toxicity, and hence, a reduced or substantially imperceptible level of side effects, than cisplatin and/or other platinum-based drugs of the art. Still further, by virtue of the inherent luminescence possessed by the rhenium(I) ion, the complexes described herein advantageously permit imaging of the rhenium complex in a living organism or intracellularly, which can be used in determining the biodistribution and patient dosage-response profile of the complex.

BRIEF DESCRIPTION OF THE DRAWINGS

FIG. 2 also shows HeLa cells stained with MitoTracker Red and Hoechst dye cotreated with TRIP (5 μM) and Mdivi-1 (50 μM) for 0 and 30 minutes (left and right bottom panels, respectively). Scale bar=10 μm.

FIG. 3A shows dose-response curve of A2780 cells treated with TRIP in the presence of 25 μM salubrinal (solid line) or absence of salubrinal (dashed line). FIG. 3B shows a Western blot of untreated (−), cisplatin (C, 10 μM), TRIP (5 μM), or bortezomib (B, 25 nM) for 24 hours in A2780 cells. FIG. 3C shows a Western blot of A2780 cells incubated with TRIP (5 μM) over 0, 0.5, 1, 1.5, and 2 hours with puromycin (10 min, left blot) and A2780 cells untreated (−), cisplatin (C, 10 μM), TRIP (5 μM), or bortezomib (B, 25 nM) treated for 24 hours with puromycin (10 min, right blot). FIG. 3D, top two panels, are confocal microscopy images of HeLa cells treated with ThT (5 μM) at 0 and 30 minutes (left and right, respectively) in the absence of TRIP (5 μM); FIG. 3D, bottom two panels, are confocal microscopy images of HeLa cells treated with ThT (5 μM) at 0 and 30 minutes (left and right, respectively) in the presence of TRIP (5 μM). Scale bar=50 μm.

DETAILED DESCRIPTION

Figure 1:
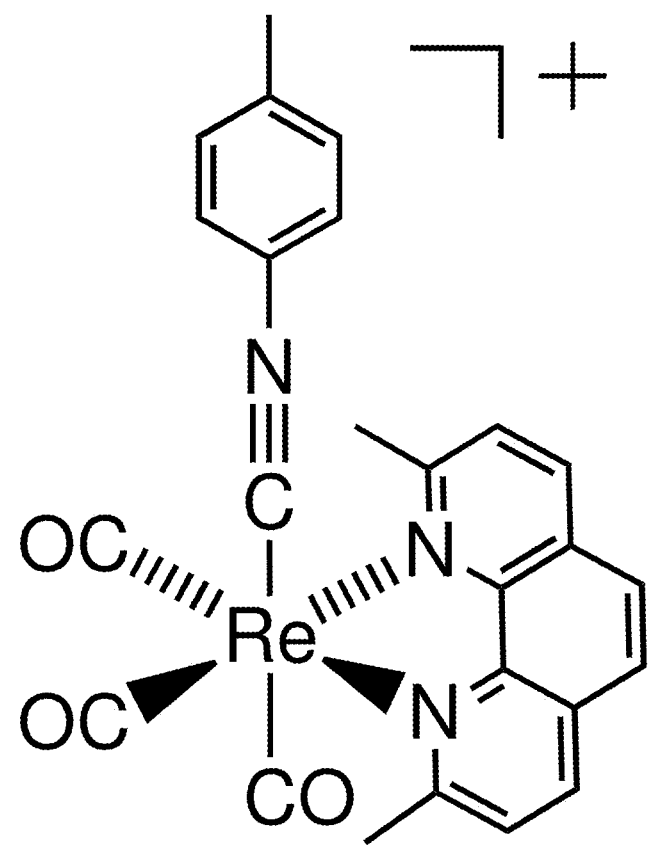
FIG. 1 shows the chemical structure of [Re(CO)$_3$(dmphen)(p-tol-ICN)]Cl (TRIP).

As used herein, the term "hydrocarbon group" (also denoted by the group R) is, in a first embodiment, composed solely of carbon and hydrogen. In different embodiments, one or more of the hydrocarbon groups can contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, or twenty carbon atoms, or a number of carbon atoms within a particular range bounded by any two of the foregoing carbon numbers. Hydrocarbon groups in different compounds described herein, or in different positions of a compound, may possess the same or different number (or preferred range thereof) of carbon atoms in order to independently adjust or optimize the activity or other characteristics of the compound.

The hydrocarbon groups (R) can be, for example, saturated and straight-chained (i.e., straight-chained alkyl groups). Some examples of straight-chained alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups.

The hydrocarbon groups (R) can alternatively be saturated and branched (i.e., branched alkyl groups). Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 20 carbon atoms, wherein the "1-yl" suffix represents the point of attachment of the group.

The hydrocarbon groups (R) can alternatively be saturated and cyclic (i.e., cycloalkyl groups). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

The hydrocarbon groups (R) can alternatively be unsaturated and straight-chained (i.e., straight-chained olefinic or alkenyl groups). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous other straight-chained alkenyl groups having up to 20 carbon atoms.

The hydrocarbon groups (R) can alternatively be unsaturated and branched (i.e., branched olefinic or alkenyl groups). Some examples of branched olefinic groups include propen-2-yl ($CH_2$=C.—$CH_3$), 1-buten-2-yl ($CH_2$=C.—$CH_2$—$CH_3$), 1-buten-3-yl ($CH_2$=CH—CH.—$CH_3$), 1-propen-2-methyl-3-yl ($CH_2$=C($CH_3$)—$CH_2$—), 1-penten-4-yl, 1-penten-3-yl, 1-penten-2-yl, 2-penten-2-yl, 2-penten-3-yl, 2-penten-4-yl, and 1,4-pentadien-3-yl, wherein the dot in any of the foregoing groups indicates a point of attachment.

The hydrocarbon groups (R) can alternatively be unsaturated and cyclic (i.e., cycloalkenyl groups). The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems.

One or more of the hydrocarbon groups (R) may (i.e., optionally) be substituted with (i.e., include) one or more heteroatoms, which are non-carbon non-hydrogen atoms. Some examples of heteroatoms include oxygen (O), nitrogen (N), sulfur (S), and halogen (halide) atoms. Some examples of halogen atoms include fluorine, chlorine, bromine, and iodine. In some embodiments, the heteroatom inserts between at least two carbon atoms (as in —C—O—C— ether, —C—S—C— thioether, —C—N(R)—C— tertiary amine, or —C=N—C— imine) or between at least one carbon atom and at least one hydrogen atom (as in —C—OH, —C—SH, —C—$NH_2$, —C—NH—C—, or —C(=NH)C—), wherein the shown carbon atom in each case can be considered part of a hydrocarbon group R described above. In other embodiments, the heteroatom replaces one or more hydrogen atoms and/or one or more carbon atoms in the hydrocarbon group, as in halogen-substituted groups (e.g., a —$CH_2F$, —$CHF_2$, and —$CF_3$) and carbonyl-substituted groups, such as ketone and aldehyde groups. In some embodiments, the hydrocarbon is substituted with multiple oxygen atoms to result in a dialkyleneoxide or polyalkyleneoxide group, such as a diethyleneoxide or polyethyleneoxide group. In the case of nitrogen or sulfur substitution, the nitrogen or sulfur atom may be bonded to a sufficient number of groups to make it positively charged, as in an ammonium group (e.g., —$NR'_3{}^+$) or sulfonium group (e.g., —$SR'_2{}^+$), in which case the positively charged moiety is necessarily associated with a counteranion (wherein R' independently represents hydrogen atom or any of the hydrocarbon groups described above). Likewise, a heteroatom may bear a negative charge, as in a deprotonated carboxy, thiocarboxy, sulfonate, phosphonate, hydroxy, or thiol group, in which case the negatively charged moiety is necessarily associated with a counter-cation.

When two or more same or different heteroatoms are bound to each other or located on the same carbon atom, the resulting group containing the heteroatoms is herein referred to as a "heteroatom-containing group". Thus, substitution with one or more heteroatoms also includes heteroatom-containing groups, unless otherwise specified. Some examples of heteroatom-containing groups include carboxy (—C(O)OR" or —OC(O)R"), thiocarboxy (—C(S)OR" or —OC(S)R"), carboxamide (—C(O)$NR"_2$, —C(O)NR"—, or —N(R")C(O)—), urea (—NR"—C(O)—$NR"_2$ or —NR"—C(O)—NR"—), thiourea (—NR"—C(S)—$NR"_2$ or —NR"—C(S)—NR"—), carbamate (—NR"—C(O)—OR", —OC(O)—$NR"_2$, or —NR"—C(O)—O—), thiocarbamate (—NR"—C(S)—OR", —OC(S)—$NR"_2$, or —NR"—C(S)—O—), nitro ($NO_2$), nitrile (CN), sulfonyl (—$S(O)_2$R" or —$S(O)_2$—), sulfinyl (i.e., sulfoxide, —S(O)R" or —S(O)—), disulfide (—C—S—S—C—), sulfonate (—$S(O)_2$R"), and amine oxide (as typically found in a nitrogen-containing ring), wherein R" independently represents hydrogen atom or any of the hydrocarbon groups (R) described above. For example, —C(O)OR" includes carboxylic acid (—C(O)OH) and carboxylic ester (—C(O)OR), where R is any of the hydrocarbon groups described above. The heteroatom-containing group may also either insert between carbon atoms or between a carbon atom and hydrogen atom, if applicable, or replace one or more hydrogen and/or carbon atoms.

In some embodiments, the hydrocarbon group (R) is substituted with one or more halogen atoms to result in a partially halogenated or perhalogenated hydrocarbon group. Some examples of partially halogenated hydrocarbon groups include —$CHY_2$, —$CH_2Y$, —$CH_2CY_3$, —CH$(CY_3)_2$, or a halo-, dihalo-, trihalo-, or tetrahalo-substituted phenyl group, wherein Y represents any of F, Cl, Br, or I, and more commonly F or Cl. Some examples of perhalogenated hydrocarbon groups include —$CY_3$, —$CY_2CY_3$, —$CY_2CY_2CY_3$, —$CY(CY_3)_2$, or perhalophenyl (—$C_6Y_5$).

In some embodiments, the hydrocarbon group (R) is, or includes, a cyclic or polycyclic (i.e., bicyclic, tricyclic, or higher cyclic) saturated or unsaturated (e.g., aliphatic or aromatic) hydrocarbon group that includes at least one ring heteroatom, such as one, two, three, four, or higher number of ring heteroatoms. Such heteroatom-substituted cyclic hydrocarbon groups are referred to herein as "heterocyclic groups". As used herein, a "ring heteroatom" is an atom other than carbon and hydrogen (typically, selected from nitrogen, oxygen, and sulfur) that is inserted into or replaces a ring carbon atom in a hydrocarbon ring structure. In some embodiments, the heterocyclic group is saturated. In other embodiments, the heterocyclic group is unsaturated, i.e., aliphatic or aromatic heterocyclic groups, wherein the aromatic heterocyclic group is also referred to herein as a "heteroaromatic ring", or a "heteroaromatic fused-ring system" in the case of at least two fused rings, at least one of which contains at least one ring heteroatom.

Some examples of saturated heterocyclic groups containing at least one oxygen atom include oxetane, tetrahydrofuran, tetrahydropyran, 1,4-dioxane, 1,3-dioxane, and 1,3-dioxepane rings. Some examples of saturated heterocyclic groups containing at least one nitrogen atom include pyrrolidine, piperidine, piperazine, imidazolidine, azepane, and decahydroquinoline rings. Some examples of saturated heterocyclic groups containing at least one sulfur atom include tetrahydrothiophene, tetrahydrothiopyran, 1,4-dithiane, 1,3-dithiane, and 1,3-dithiolane rings. Some examples of saturated heterocyclic groups containing at least one oxygen atom and at least one nitrogen atom include morpholine and oxazolidine rings. An example of a saturated heterocyclic group containing at least one oxygen atom and at least one sulfur atom includes 1,4-thioxane. An example of a saturated heterocyclic group containing at least one nitrogen atom and at least one sulfur atom includes thiazolidine and thiamorpholine rings.

Some examples of unsaturated heterocyclic groups containing at least one oxygen atom include furan, pyran, 1,4-dioxin, benzofuran, dibenzofuran, and dibenzodioxin rings. Some examples of unsaturated heterocyclic groups containing at least one nitrogen atom include pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings. Some examples of unsaturated heterocyclic groups containing at least one sulfur atom include thiophene, thianaphthene, benzothiophene, thiochroman, and thiochromene rings. Some examples of unsaturated heterocyclic groups containing at least one oxygen atom and at least one nitrogen atom include oxazole, isoxazole, benzoxazole, benzisoxazole, oxazoline, 1,2,5-oxadiazole (furazan), and 1,3,4-oxadiazole rings. Some examples of unsaturated heterocyclic groups containing at least one nitrogen atom and at least one sulfur atom include thiazole, isothiazole, benzothiazole, benzoisothiazole, thiazoline, and 1,3,4-thiadiazole rings.

In some embodiments, any of the generic substituents (e.g., R, R', $R^a$, and the like) described below may independently exclude any one or more of the classes, subclasses, or particular hydrocarbon groups described above, or may independently include only specific hydrocarbon groups selected from the hydrocarbon groups (R) described above.

Generally, the heteroatoms, if present on an R, R', or $R^a$ group, do not engage in additional coordination to the Re. Thus, generally, the heteroatoms, if present on an R, R', or $R^a$ group, are non-coordinating to the Re. For this reason, amino-containing groups (e.g., —NR'$_2$ or —C(O)NR'$_2$ groups) are generally not included in an R, R', or $R^a$ group. Such groups also have the propensity to form coordination polymers of Re, which are not considered here.

In a first aspect, the present disclosure is directed to rhenium(I) complexes and compositions containing these complexes. The term "rhenium(I)" refers to a rhenium ion having a +1 charge. The rhenium(I) ion is hexa-coordinate and bound to only neutral (uncharged) ligands. The term "uncharged" indicates that the ligand is not charged (i.e., not anionic or cationic) either inherently in the atoms making the core ring structure or as groups appended to the core ring structure. The term "ligand" refers to a molecule that engages in a coordination bond to the rhenium(I) ion. Two of the six coordination sites of the rhenium(I) are occupied by a bidentate ligand. The bidentate ligand contains at least one ring containing a ring nitrogen atom bound to the rhenium(I), and the bidentate ligand contains another nitrogen atom, either in a ring or not in a ring, bound to the rhenium(I). The remaining coordination sites on the rhenium (i.e., those sites not occupied by the bidentate ligand) are occupied by one or more of CO, neutral phosphine molecules, solvent molecules, and isonitrile ligands of the formula —CN—R, wherein R is an aliphatic or aromatic hydrocarbon group containing 1-20 carbon atoms, as described above, provided that at least one of the remaining coordination sites is occupied by an isonitrile ligand. In some embodiments, the isonitrile ligand is in an axial position. The term "axial," as used herein, refers to a coordination site on the rhenium(I) coordination sphere that is perpendicular to the plane of the bidentate bicyclic ligand. As the ligands are neutral, the rhenium(I)-ligand coordination sphere has a +1 charge. For purposes of the present invention, the counteranion is non-coordinating, and typically monovalent (i.e., having a charge of −1).

More specifically, the rhenium(I) complex has the following structure:

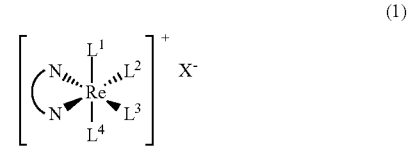

In Formula (1) above,

represents an uncharged bidentate ligand with two nitrogen atoms bound to the rhenium ion. As discussed above, the bidentate ligand contains at least one ring nitrogen atom bound to the rhenium. The bidentate ligand contains a ring containing a ring nitrogen atom bound to the rhenium(I), and the bidentate ligand contains another nitrogen atom, either in a ring or not in a ring, bound to the rhenium(I). In some embodiments, the bidentate ligand contains at least two rings, with one or two of the rings containing a ring nitrogen atom. In the event the bidentate ligand contains only one ring containing a ring nitrogen atom, the bidentate ligand contains another nitrogen atom, not within a ring, that also binds to the rhenium. The bidentate ligand may contain any number of rings (e.g., two, three, four, five, or six), wherein the rings may be connected by one or more covalent bonds and/or one or more of the rings may be fused to each other. Thus, the bidentate ligand may be, for example, bicyclic, tricyclic, or tetracyclic.

In some embodiments,

possesses a saturated bicyclic ring system, e.g., 2,2'-bipiperidine. In other embodiments,

possesses an unsaturated bicyclic ring system, which may be an aliphatic bicyclic ring system or aromatic (i.e., heteroaromatic) bicyclic ring system, e.g., a bipyridine, phenanthroline, or naphthyridine ring system.

In some embodiments,

is unsubstituted on its rings. The term "unsubstituted" means that only hydrogen atoms are present on (i.e., bound to) ring carbon atoms. In other embodiments,

is substituted on one, two, or more rings, with one or more substituents. The term "substituted" means that at least one substituent (atom or group) other than a hydrogen atom is present on at least one of the ring carbon atoms. The substituent(s) can be independently selected from, for example: (i) hydrocarbon group (R') containing 1-6 carbon atoms, as described above, as a selection of hydrocarbon groups (R); (ii) —OR$^a$ groups; (iii) —C(O)OR$^a$ groups; (iv) —OC(O)R$^a$ groups; (v) —C(O)R$^a$ groups; (vi) —NR$^a_2$ groups; (vii) —C(O)NR$^a_2$ groups; (viii) —NR$^a$C(O)R$^a$ groups; (ix) halogen atoms, (x) —CN groups, and (xi) nitro (NO$_2$) groups, wherein the hydrocarbon groups R' optionally include one or more heteroatoms selected from oxygen, nitrogen, sulfur, and halogen atoms, or heteroatom-containing groups containing one or more such heteroatoms, and R$^a$ is independently selected from hydrogen atoms and hydrocarbon groups R' and also optionally contains one or more heteroatoms as discussed above. Some examples of —OR' groups, in particular, include methoxy, ethoxy, n-propoxy, isopropoxy, n-butoxy, isobutoxy, sec-butoxy, t-butoxy, n-pentoxy, isopentoxy, n-hexoxy, and isohexoxy groups.

In a first set of embodiments,

in Formula (1) has the following structure, which contains a 2,2'-bipyridine core:

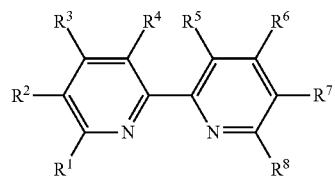

(2)

In Formula (2) above, $R^1$, $R^2$, $R^3$, $R^4$, $R^5$, $R^6$, $R^7$, and $R^8$ are independently selected from hydrogen atoms; hydrocarbon groups (R') containing 1-6 carbon atoms; —OR" groups; —C(O)OR" groups; —OC(O)R" groups; —C(O)R" groups; —NR"$_2$ groups; —C(O)NR"$_2$ groups; —NR"C(O)R" groups; halogen atoms, —CN groups; and nitro groups, wherein the hydrocarbon groups (R') optionally include one or more heteroatoms selected from oxygen, nitrogen, and sulfur, and R" is independently selected from hydrogen atoms and hydrocarbon groups (R'). In some embodiments, $R^1$, $R^2$, $R^3$, $R^4$, $R^5$, $R^6$, $R^7$, and $R^8$ are all hydrogen atoms. In other embodiments, precisely or at least one, two, three, or four of $R^1$, $R^2$, $R^3$, $R^4$, $R^5$, $R^6$, $R^7$, and $R^8$ are not hydrogen atoms. For example, precisely or at least one, two, three, or four of $R^1$, $R^2$, $R^3$, $R^4$, $R^5$, $R^6$, $R^7$, and $R^8$ are independently hydrocarbon groups (R), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms; or independently —CN groups, or independently nitro groups, or independently selected from a combination of any of the foregoing types of groups. In some embodiments, nitrogen-containing or amino-containing groups are excluded. Thus, in some embodiments, precisely or at least one, two, three, or four of $R^1$, $R^2$, $R^3$, $R^4$, $R^5$, $R^6$, $R^7$, and $R^8$ may be independently selected from hydrogen atoms; hydrocarbon groups (R') containing 1-6 carbon atoms (or more specifically, alkyl groups); —OR" groups; —C(O)OR" groups; —OC(O)R" groups; —C(O)R" groups; and halogen atoms, or selected from a sub-set of these. In some embodiments, at least one, two, three, or four of $R^1$, $R^2$, $R^3$, $R^4$, $R^5$, $R^6$, $R^7$, and $R^8$ are independently selected from hydrocarbon groups (R') containing 1-6 carbon atoms; —OR" groups; —C(O)OR" groups; —OC(O)R" groups; and —C(O)R" groups.

In some embodiments of Formula (2), at least one or two of $R^1$, $R^2$, $R^3$, and $R^4$ are not hydrogen atoms and at least one or two of $R^5$, $R^6$, $R^7$, and $R^8$ are not hydrogen atoms, e.g., at least one or two of $R^1$, $R^2$, $R^3$, and $R^4$ are independently selected from any of the groups provided above other than hydrogen, and at least one or two of $R^5$, $R^6$, $R^7$, and $R^8$ are independently selected from any of the groups provided above other than hydrogen. In more specific embodiments, at least $R^1$ and $R^8$, or at least $R^2$ and $R^7$, or at least $R^3$ and $R^6$, or at least $R^4$ and $R^5$, or a combination thereof are not hydrogen atoms and are independently selected from any of the groups provided above, i.e., independently hydrocarbon groups (R'), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms, or independently —CN groups, or independently nitro groups, or independently selected from two, three, four, or five of any of the foregoing types of groups. In some embodiments, at least $R^1$ and $R^8$, or at least $R^2$ and $R^7$, or at least $R^3$ and $R^6$, or at least $R^4$ and $R^5$, or a combination thereof are independently selected from hydrocarbon groups (R') containing 1-6 carbon atoms; —OR" groups; —C(O)OR" groups; —OC(O)R" groups; and —C(O)R" groups, or a subset thereof. In further specific embodiments, at least $R^1$ and $R^8$, or at least $R^2$ and $R^7$, or at least $R^3$ and $R^6$, or at least $R^4$ and $R^5$, or a combination thereof are selected from (i) straight-chained and/or branched alkyl groups (R''') having 1-6 or 1-4 carbon atoms (e.g., methyl, ethyl, n-propyl, isopropyl, n-butyl, isobutyl, sec-butyl, and t-butyl), and phenyl groups, (ii) —OR''' (and phenoxy) groups, (iii) —C(O)OR''' groups, (iv) —OC(O)R''' groups, and/or (v) —C(O)R''' groups, wherein a phenyl group may replace R''' in each instance, and the phenyl group may or may not contain one or more substituents, such as methyl or methoxy groups, as discussed above.

In Formula (2), any two $R^1$, $R^2$, $R^3$, $R^4$, $R^5$, $R^6$, $R^7$, and $R^8$ groups adjacent from each other may interconnect to form a ring. Moreover, the interconnection may be saturated or unsaturated. For example, $R^4$ and $R^5$ can be taken as methyl groups and the methyl groups interconnected with formation of a carbon-carbon double bond and loss of four hydrogen atoms so as to form a phenanthroline structure. Alternatively, for example, $R^1$ and $R^2$ may interconnect to form a benzene ring and $R^7$ and $R^8$ may likewise interconnect to form a benzene ring, in which case the structure of Formula (2) corresponds to a bisquinoline structure having the following structure:

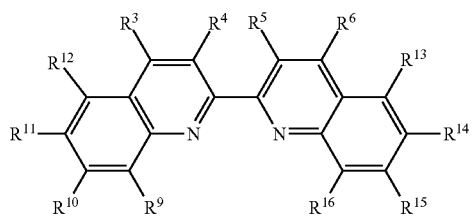

(2a)

In Formula (2a) above, $R^3$, $R^4$, $R^5$, and $R^6$ retain their definitions provided earlier above under Formula (2), and the $R^9$, $R^{10}$, $R^{11}$, $R^{12}$, $R^{13}$, $R^{14}$, $R^{15}$, and $R^{16}$ groups are independently selected from any of the groups or sub-sets thereof as provided above, e.g., independently selected from hydrogen atoms; hydrocarbon groups (R') containing 1-6 carbon atoms, or more specifically, alkyl groups R'''; —OR'' or —OR''' groups; —C(O)OR'' or —C(O)OR''' groups; —OC(O)R'' or —OC(O)R''' groups; —C(O)R'' or —C(O)R''' groups; —NR''$_2$ groups; —C(O)NR''$_2$ groups; —NR''C(O)R'' groups; halogen atoms, —CN groups, and nitro groups, or they may be independently selected from a subset thereof, particularly those groups not containing nitrogen atoms. In some embodiments, $R^3$, $R^4$, $R^5$, $R^6$, $R^9$, $R^{10}$, $R^{11}$, $R^{12}$, $R^{13}$, $R^{14}$, $R^{15}$, and $R^{16}$ groups are all hydrogen atoms. In other embodiments, one, two, three, or four of $R^3$, $R^4$, $R^5$, $R^6$, $R^9$, $R^{10}$, $R^{11}$, $R^{12}$, $R^{13}$, $R^{14}$, $R^{15}$, and $R^{16}$ groups are not hydrogen atoms and are selected from any of the non-hydrogen groups provided above, particularly those groups not containing nitrogen atoms. In more specific embodiments, only or at least $R^9$ and $R^{16}$ and/or $R^{12}$ and $R^{13}$ are not hydrogen atoms and are selected from any of the non-hydrogen groups provided above, particularly those groups not containing nitrogen atoms.

Alternatively, for example, $R^2$ and $R^3$ in Figure (2) may interconnect to form a benzene ring and $R^6$ and $R^7$ may likewise interconnect to form a benzene ring, in which case the structure of Formula (2) corresponds to a bisquinoline structure having the following structure:

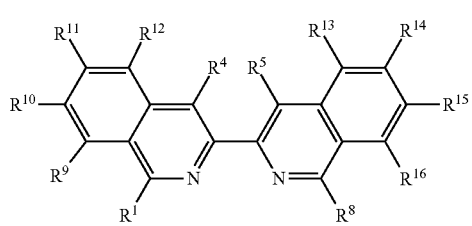

(2b)

In Formula (2b) above, $R^1$, $R^4$, $R^5$, and $R^8$ retain their definitions provided earlier above under Formula (2), and the $R^9$, $R^{10}$, $R^{11}$, $R^{12}$, $R^{13}$, $R^{14}$, $R^{15}$, and $R^{16}$ groups are defined as provided under Formula (2a). In some embodiments, $R^1$, $R^4$, $R^5$, $R^8$, $R^9$, $R^{10}$, $R^{11}$, $R^{12}$, $R^{13}$, $R^{14}$, $R^{15}$, and $R^{16}$ groups are all hydrogen atoms. In other embodiments, one, two, three, or four of $R^1$, $R^4$, $R^5$, $R^8$, $R^9$, $R^{10}$, $R^{11}$, $R^{12}$, $R^{13}$, $R^{14}$, $R^{15}$, and $R^{16}$ groups are not hydrogen atoms and are selected from any of the non-hydrogen groups provided above, particularly those groups not containing nitrogen atoms. In more specific embodiments, only or at least $R^1$ and $R^8$ and/or $R^9$ and $R^{16}$ and/or $R^{10}$ and $R^{15}$ and/or $R^{11}$ and $R^{14}$ and/or $R^{12}$ and $R^{13}$ are not hydrogen atoms and are selected from any of the non-hydrogen groups provided above, particularly those groups not containing nitrogen atoms.

In another particular set of embodiments,

in Formula (1) has the following structure, which contains a phenanthroline core:

(3)

In Formula (3) above, $R^{1a}$, $R^{2a}$, $R^{3a}$, $R^{4a}$, $R^{5a}$, $R^{6a}$, $R^{7a}$, and $R^{8a}$ are independently selected from hydrogen atoms; hydrocarbon groups (R') containing 1-6 carbon atoms; —OR'' groups; —C(O)OR'' groups; —OC(O)R'' groups; —C(O)R'' groups; —NR''$_2$ groups; —C(O)NR''$_2$ groups; —NR''C(O)R'' groups; halogen atoms, —CN groups, and nitro groups, wherein the hydrocarbon groups (R') optionally include one or more heteroatoms selected from oxygen, nitrogen, and sulfur, and R'' is independently selected from hydrogen atoms and hydrocarbon groups (R'). In some embodiments, $R^{1a}$, $R^{2a}$, $R^{3a}$, $R^{4a}$, $R^{5a}$, $R^{6a}$, $R^{7a}$, and $R^{8a}$ are all hydrogen atoms. In other embodiments, precisely or at least one, two, three, or four of $R^{1a}$, $R^{2a}$, $R^{3a}$, $R^{4a}$, $R^{5a}$, $R^{6a}$, $R^{7a}$, and $R^{8a}$ are not hydrogen atoms. For example, precisely or at least one, two, three, or four of $R^{1a}$, $R^{2a}$, $R^{3a}$, $R^{4a}$, $R^{5a}$, $R^{6a}$, $R^{7a}$, and $R^{8a}$ are independently hydrocarbon groups (R'), or independently —OR'' groups, or independently —C(O)OR'' groups; or independently —OC(O)R'' groups; or independently —C(O)R'' groups; or independently —NR''$_2$ groups; or independently —C(O)NR''$_2$ groups; or independently —NR''C(O)R'' groups; or independently halogen atoms; or independently —CN groups, or independently nitro groups, or independently selected from a combination of any of the foregoing types of groups. In some embodiments, nitrogen-containing or amino-containing groups are excluded. Thus, precisely or at least one, two, three, or four of $R^{1a}$, $R^{2a}$, $R^{3a}$, $R^{4a}$, $R^{5a}$, $R^{6a}$, $R^{7a}$, and $R^{8a}$ may be independently selected from hydrogen atoms; hydrocarbon groups (R') containing 1-6 carbon atoms (or more specifically, alkyl groups); —OR'' groups; —C(O)OR'' groups; —OC(O)R'' groups; —C(O)R'' groups; and halogen atoms, or selected from a sub-set of these. In some embodiments, at least one, two, three, or four of $R^{1a}$, $R^{2a}$, $R^{3a}$, $R^{4a}$, $R^{5a}$, $R^{6a}$, $R^{7a}$, and $R^{8a}$ are independently selected from hydrocarbon groups (R') containing 1-6 carbon atoms; —OR" groups; —C(O)OR" groups; —OC(O)R" groups; and —C(O)R" groups.

In some embodiments of Formula (3), at least one or two of $R^{1a}$, $R^{2a}$, and $R^{3a}$ are not hydrogen atoms and at least one or two of $R^{6a}$, $R^{7a}$, and $R^{8a}$ are not hydrogen atoms, e.g., at least one or two of $R^{1a}$, $R^{2a}$, and $R^{3a}$ are independently selected from any of the groups provided above other than hydrogen, and at least one or two of $R^{6a}$, $R^{7a}$, and $R^{8a}$ are independently selected from any of the groups provided above other than hydrogen. In more specific embodiments, at least $R^{1a}$ and $R^{8a}$, or at least $R^{2a}$ and $R^{7a}$, or at least $R^{3a}$ and $R^{6a}$, or at least $R^{4a}$ and $R^{5a}$, or a combination thereof are not hydrogen atoms and are independently selected from any of the groups provided above, i.e., independently hydrocarbon groups (R'), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms; or independently —CN groups, or independently nitro groups, or independently selected from two, three, four, or five of any of the foregoing types of groups. In some embodiments, at least $R^{1a}$ and $R^{8a}$, or at least $R^{2a}$ and $R^{7a}$, or at least $R^{3a}$ and $R^{6a}$, or at least $R^{4a}$ and $R^{5a}$, or a combination thereof are independently selected from hydrocarbon groups (R') containing 1-6 carbon atoms; —OR" groups; —C(O)OR" groups; —OC(O)R" groups; —C(O)R" groups, and halogen atoms, or a subset thereof. In further specific embodiments, at least $R^{1a}$ and $R^{8a}$, or at least $R^{2a}$ and $R^{7a}$, or at least $R^{3a}$ and $R^{6a}$, or at least $R^{4a}$ and $R^{5a}$, or a combination thereof are selected from (i) straight-chained and/or branched alkyl groups (R''') having 1-6 or 1-4 carbon atoms (e.g., methyl, ethyl, n-propyl, isopropyl, n-butyl, isobutyl, sec-butyl, and t-butyl), and phenyl groups, (ii) —OR''' (and phenoxy) groups, (iii) —C(O)OR''' groups, (iv) —OC(O)R''' groups, and/or (v) —C(O)R''' groups, wherein a phenyl group may replace R''' in each instance, and the phenyl group may or may not contain one or more substituents, such as methyl or methoxy groups, as discussed above.

In Formula (3), any two $R^{1a}$, $R^{2a}$, $R^{3a}$, $R^{4a}$, $R^{5a}$, $R^{6a}$, $R^{7a}$, and $R^{8a}$ groups adjacent from each other may interconnect to form a ring. Moreover, the interconnection may be saturated or unsaturated. For example, $R^{1a}$ and $R^{2a}$ may interconnect to form a benzene ring and $R^{7a}$ and $R^{8a}$ may likewise interconnect to form a benzene ring, in which case the structure of Formula (3) corresponds to a dibenzo[b,j][1,10]phenanthroline structure. Alternatively, for example, $R^{2a}$ and $R^{3a}$ may interconnect to form a benzene ring and $R^{6a}$ and $R^{7a}$ may likewise interconnect to form a benzene ring, in which case the structure of Formula (3) corresponds to a dibenzo[c,i][1,10]phenanthroline. Moreover, the interconnected portions may or may not be substituted on one or more of the ring carbon atoms by any of the groups provided above.

In another particular set of embodiments,

in Formula (1) has the following structure, which contains a 1,8-naphthyridine core:

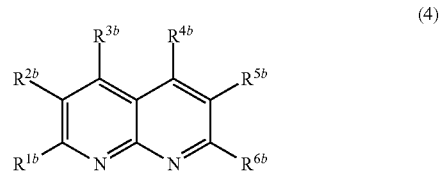

(4)

In Formula (4) above, $R^{1b}$, $R^{2b}$, $R^{3b}$, $R^{4b}$, $R^{5b}$, and $R^{6b}$ are independently selected from hydrogen atoms; hydrocarbon groups (R') containing 1-6 carbon atoms; —OR" groups; —C(O)OR" groups; —OC(O)R" groups; —C(O)R" groups; —NR"$_2$ groups; —C(O)NR"$_2$ groups; —NR"C(O)R" groups; halogen atoms, —CN groups, and nitro groups, wherein the hydrocarbon groups (R') optionally include one or more heteroatoms selected from oxygen, nitrogen, and sulfur, and R" is independently selected from hydrogen atoms and hydrocarbon groups (R'). In some embodiments, $R^{1b}$, $R^{2b}$, $R^{3b}$, $R^{4b}$, $R^{5b}$, and $R^{6b}$ are all hydrogen atoms. In other embodiments, precisely or at least one, two, three, or four of $R^{1b}$, $R^{2b}$, $R^{3b}$, $R^{4b}$, $R^{5b}$, and $R^{6b}$ are not hydrogen atoms. For example, precisely or at least one, two, three, or four of $R^{1b}$, $R^{2b}$, $R^{3b}$, $R^{4b}$, $R^{5b}$, and $R^{6b}$ are independently hydrocarbon groups (R'), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms; or independently —CN groups, or independently nitro groups, or independently selected from a combination of any of the foregoing types of groups. In some embodiments, nitrogen-containing or amino-containing groups are excluded. Thus, precisely or at least one, two, three, or four of $R^{1b}$, $R^{2b}$, $R^{3b}$, $R^{4b}$, $R^{5b}$, and $R^{6b}$ may be independently selected from hydrogen atoms; hydrocarbon groups (R') containing 1-6 carbon atoms (or more specifically, alkyl groups); —OR" groups; —C(O)OR" groups; —OC(O)R" groups; —C(O)R" groups; and halogen atoms, or selected from a sub-set of these. In some embodiments, at least one, two, three, or four of $R^{1b}$, $R^{2b}$, $R^{3b}$, $R^{4b}$, $R^{5b}$, and $R^{6b}$ are independently selected from hydrocarbon groups (R') containing 1-6 carbon atoms; —OR" groups; —C(O)OR" groups; —OC(O)R" groups; and —C(O)R" groups.

In some embodiments of Formula (4), at least one or two of $R^{1b}$, $R^{2b}$, and $R^{3b}$ are not hydrogen atoms and at least one or two of $R^{4b}$, $R^{5b}$, and $R^{6b}$ are not hydrogen atoms, e.g., at least one or two of $R^{1b}$, $R^{2b}$, and $R^{3b}$ are independently selected from any of the groups provided above other than hydrogen, and at least one or two of $R^{4b}$, $R^{5b}$, and $R^{6b}$ are independently selected from any of the groups provided above other than hydrogen. In more specific embodiments, at least $R^{1b}$ and $R^{6b}$, or at least $R^{2b}$ and $R^{5b}$, or at least $R^{3b}$ and $R^{4b}$, or a combination thereof are not hydrogen atoms and are independently selected from any of the groups provided above, i.e., independently hydrocarbon groups (R'), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms, or independently —CN groups, or independently nitro groups, or independently selected from two, three, four, or five of any of the foregoing types of groups. In some embodiments, at least $R^{1b}$ and $R^{6b}$, or at least $R^{2b}$ and $R^{5b}$, or at least $R^{3b}$ and $R^{4b}$, or a combination thereof are independently selected from hydrocarbon groups (R') containing 1-6 carbon atoms; —OR" groups; —C(O)OR" groups; —OC(O)R" groups; and —C(O)R" groups, or a subset thereof. In further specific embodiments, at least $R^{1b}$ and $R^{6b}$, or at least $R^{2b}$ and $R^{5b}$, or at least $R^{3b}$ and $R^{4b}$, or a combination thereof are selected from (i) straight-chained and/or branched alkyl groups (R''') having 1-6 or 1-4 carbon atoms (e.g., methyl, ethyl, n-propyl, isopropyl, n-butyl, isobutyl, sec-butyl, and t-butyl), and phenyl groups, (ii) —OR''' (and phenoxy) groups, (iii) —C(O)OR''' groups, (iv) —OC(O)R''' groups, and/or (v) —C(O)R''' groups, wherein a phenyl group may replace R''' in each instance, and the phenyl group may or may not contain one or more substituents, such as methyl or methoxy groups, as discussed above.

In Formula (4), any two $R^{1b}$, $R^{2b}$, $R^{3b}$, $R^{4b}$, $R^{5b}$, and $R^{6b}$ groups adjacent from each other may interconnect to form a ring. Moreover, the interconnection may be saturated or unsaturated. For example, $R^{1b}$ and $R^{2b}$ may interconnect to form a benzene ring and $R^{5b}$ and $R^{6b}$ may likewise interconnect to form a benzene ring, in which case the structure of Formula (4) corresponds to a dibenzo[b,g][1,8]naphthyridine structure. Alternatively, for example, $R^{2b}$ and $R^{3b}$ may interconnect to form a benzene ring and $R^{4b}$ and $R^{5b}$ may likewise interconnect to form a benzene ring, in which case the structure of Formula (4) corresponds to a dibenzo[c,f][1,8]naphthyridine. As another example, $R^{3b}$ and $R^{4b}$ may interconnect to form a benzene ring, in which case the structure of Formula (4) corresponds to a benzo[d,e][1,8]naphthyridine (i.e., 1,9-diazaphenalene). Moreover, the interconnected portions may or may not be substituted on one or more of the ring carbon atoms by any of the groups provided above.

In another particular set of embodiments,

in Formula (1) has the following pyridyl-imino structure, which contains one ring containing a ring nitrogen atom and another nitrogen atom not in a ring:

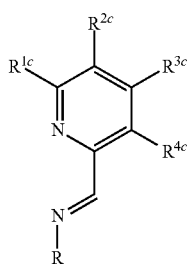

(5)

In Formula (5) above, the two shown nitrogen atoms coordinate to the rhenium(I). The groups $R^{1c}$, $R^{2c}$, $R^{3c}$, and $R^{4c}$ are independently selected from hydrogen atoms; hydrocarbon groups (R') containing 1-6 carbon atoms; —OR" groups; —C(O)OR" groups; —OC(O)R" groups; —C(O)R" groups; —NR"$_2$ groups; —C(O)NR"$_2$ groups; —NR"C(O)R" groups; halogen atoms, —CN groups, and nitro groups, wherein the hydrocarbon groups (R') optionally include one or more heteroatoms selected from oxygen, nitrogen, and sulfur, and R" is independently selected from hydrogen atoms and hydrocarbon groups (R'). In some embodiments, $R^{1c}$, $R^{2c}$, $R^{3c}$, and $R^{4c}$ are all hydrogen atoms. In other embodiments, precisely or at least one, two, three, or four (all) of $R^{1c}$, $R^{2c}$, $R^{3c}$, and $R^{4c}$ are not hydrogen atoms. For example, precisely or at least one, two, three, or four of $R^{1c}$, $R^{2c}$, $R^{3c}$, and $R^{4c}$ may independently be hydrocarbon groups (R'), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms; or independently —CN groups; or independently nitro groups, or independently selected from a combination of any of the foregoing types of groups. In some embodiments, nitrogen-containing or amino-containing groups are excluded. Thus, precisely or at least one, two, three, or four of $R^{1c}$, $R^{2c}$, $R^{3c}$, and $R^{4c}$ may be independently selected from hydrogen atoms; hydrocarbon groups (R') containing 1-6 carbon atoms (or more specifically, alkyl groups); —OR" groups; —C(O)OR" groups; —OC(O)R" groups; —C(O)R" groups; and halogen atoms, or selected from a sub-set of these. In some embodiments, at least one, two, three, or four of $R^{1c}$, $R^{2c}$, $R^{3c}$, and $R^{4c}$ are independently selected from hydrocarbon groups (R') containing 1-6 carbon atoms; —OR" groups; —C(O)OR" groups; —OC(O)R" groups; —C(O)R" groups, and halogen atoms (e.g., Cl and Br). The R group shown in Formula (5) can be any of the hydrocarbon groups (R) described above, but is more typically a cyclic group, and more typically, an unsaturated (more typically, aromatic or heteroaromatic) ring, such as any of the rings described above under the description of hydrocarbon groups (R).

In specific embodiments of Formula (5), the R group shown in Formula (5) is a phenyl ring, in which case Formula (5) can be expressed by the following formula:

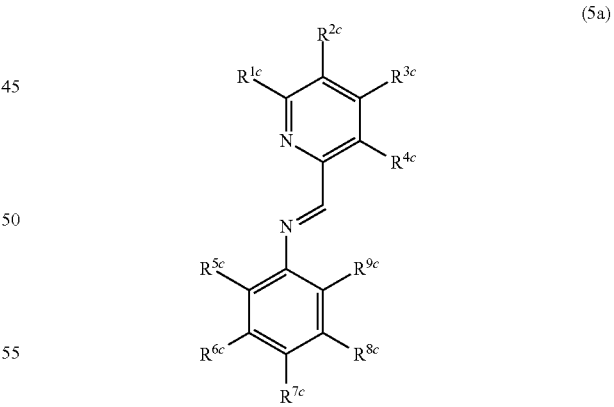

(5a)

In Formula (5a) above, $R^{1c}$, $R^{2c}$, $R^{3c}$, and $R^{4c}$ are as described above. The groups $R^{5c}$, $R^{6c}$, $R^{7c}$, $R^{8c}$, and $R^{9c}$ are independently selected from any of the groups described above for $R^{1c}$, $R^{2c}$, $R^{3c}$, and $R^{4c}$. In particular embodiments, one or two of $R^{1c}$, $R^{2c}$, $R^{3c}$, and $R^{4c}$ are independently selected from hydrocarbon groups (R') containing 1-6 carbon atoms; —NR"$_2$ groups; —C(O)NR"$_2$ groups; —NR"C(O)R" groups, —OR" groups; —C(O)OR" groups; —OC(O)R" groups; —C(O)R" groups, and halogen atoms (e.g., Cl and Br), wherein R" is independently selected from hydrogen atoms and hydrocarbon groups (R').

Some particular examples of bidentate ligands include the following:

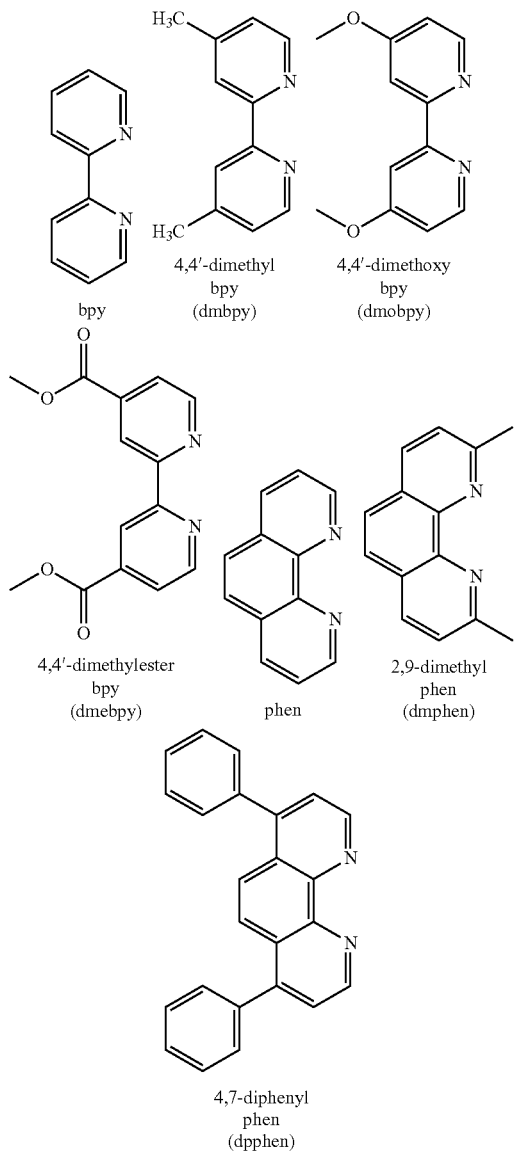

As discussed above under Formula (1), precisely or at least one of $L^1$, $L^2$, $L^3$, and $L^4$ is an isonitrile ligand of the general formula —CN—R, wherein R is an aliphatic or aromatic hydrocarbon group containing 1-20 carbon atoms, as described above. The R group in the isonitrile ligand may be, for example, any of the linear, branched, or cyclic alkyl or alkenyl groups described above under R, R', or R". In typical embodiments, R in the isonitrile ligand is a cyclic hydrocarbon group, such as any of the saturated or unsaturated cyclic hydrocarbon groups described above. The hydrocarbon group (R) in the isonitrile ligand may or may not be substituted with one, two, or three of any of the substituents provided earlier above for the bidentate ligand, i.e., substituents (i)-(xi). In specific embodiments, R in the isonitrile ligand is an aromatic ring (e.g., phenyl) or heteroaromatic ring (e.g., pyridyl).

In particular embodiments, the isonitrile ligand contains R as a phenyl ring, in which case the isonitrile group can be expressed by the following formula:

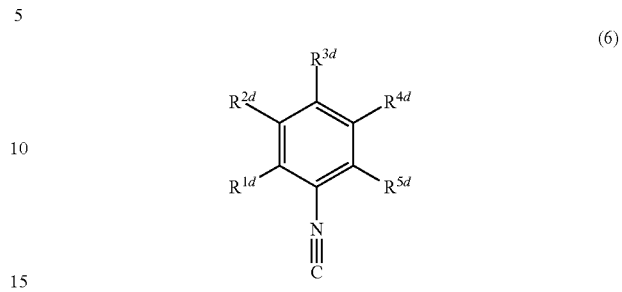

In Formula (6) above, $R^{1d}$, $R^{2d}$, $R^{3d}$, $R^{4d}$, and $R^{5d}$ are independently selected from hydrogen atoms; hydrocarbon groups (R') containing 1-6 carbon atoms; —OR" groups; —C(O)OR" groups; —OC(O)R" groups; —C(O)R" groups; —NR"$_2$ groups; —C(O)NR"$_2$ groups; —NR"C(O)R" groups; halogen atoms, —CN groups, and nitro groups, wherein the hydrocarbon groups (R') optionally include one or more heteroatoms selected from oxygen, nitrogen, and sulfur, and R" is independently selected from hydrogen atoms and hydrocarbon groups (R'). In some embodiments, $R^{1d}$, $R^{2d}$, $R^{3d}$, $R^{4d}$, and $R^{5d}$ are all hydrogen atoms. In other embodiments, precisely or at least one, two, three, or four of $R^{1d}$, $R^{2d}$, $R^{3d}$, $R^{4d}$, and $R^{5d}$ are not hydrogen atoms. For example, precisely or at least one, two, three, or four of $R^{1d}$, $R^{2d}$, $R^{3d}$, $R^{4d}$, and $R^{5d}$ may independently be hydrocarbon groups (R'), or independently —OR" groups, or independently —C(O)OR" groups; or independently —OC(O)R" groups; or independently —C(O)R" groups; or independently —NR"$_2$ groups; or independently —C(O)NR"$_2$ groups; or independently —NR"C(O)R" groups; or independently halogen atoms; or independently —CN groups, or independently nitro groups, or independently selected from a combination of any of the foregoing types of groups. In some embodiments, nitrogen-containing or amino-containing groups are excluded. Thus, precisely or at least one, two, three, or four of $R^{1d}$, $R^{2d}$, $R^{3d}$, $R^{4d}$, and $R^{5d}$ may be independently selected from hydrogen atoms; hydrocarbon groups (R') containing 1-6 carbon atoms (or more specifically, alkyl groups); —OR" groups; —C(O)OR" groups; —OC(O)R" groups; —C(O)R" groups; and halogen atoms, or selected from a sub-set of these. In some embodiments, at least one, two, three, or four of $R^{1d}$, $R^{2d}$, $R^{3d}$, $R^{4d}$, and $R^{5d}$ are independently selected from hydrocarbon groups (R') containing 1-6 carbon atoms; —OR" groups; —C(O)OR" groups; —OC(O)R" groups; —C(O)R" groups, and halogen atoms (e.g., Cl and Br). In some embodiments, only one, two, or three of $R^{1d}$, $R^{3d}$, $R^{5d}$ are selected from any of the specific selections of groups provided above.

Some particular examples of isonitrile ligands include the following:

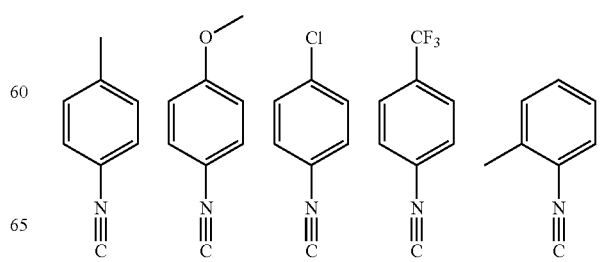

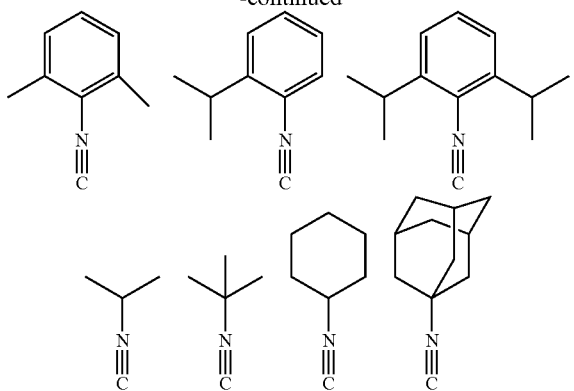

In Formula (1), any one, two, or three of the four remaining L groups that are not isonitrile groups (i.e., one, two, or three selected from $L^1$, $L^2$, $L^3$, and $L^4$) are independently selected from carbon monoxide (CO), neutral phosphine molecules, and solvent molecules. In typical embodiments, precisely or at least one of the remaining L groups (i.e., that is not an isonitrile group) is a CO molecule. In some embodiments, two or three of the remaining L groups are CO groups. Similarly, in some embodiments, precisely or at least one of the remaining L groups (i.e., that is not an isonitrile group) is a phosphine molecule. In some embodiments, two or three of the remaining L groups are phosphine molecules. In other embodiments, precisely or at least one of the remaining L groups (i.e., that is not an isonitrile group) is a solvent molecule. In some embodiments, two or three of the remaining L groups are solvent molecules. In some embodiments, none of the remaining L groups are phosphine molecules. In other embodiments, none of the remaining L groups are solvent molecules.

The phosphine ligand is any molecule known in the art of the general formula $PR^dR^eR^f$, i.e., of the following structure:

(7)

wherein $R^d$, $R^e$, and $R^f$ are independently selected from any of the hydrocarbon groups R, R', or R" described above, wherein one, two, or all of $R^d$, $R^e$, and $R^f$ optionally and independently include one or more heteroatoms (O, N, or S) or heteroatom-containing groups, as described above (e.g., by insertion between a C—C bond or by replacement of a hydrogen atom), provided that the heteroatoms, if present, do not form a coordination bond with the Re (i.e., only the phosphorus atom in the phosphine molecule coordinates with the Re). Each of $R^d$, $R^e$, and $R^f$ bond to the phosphorus atom by a carbon atom, i.e., $R^d$, $R^e$, and $R^f$ are all bound to the phosphorus atom by a P—C bond. The phosphine considered herein should also be a stable phosphine, i.e., it should not be reactive with water or oxygen to form a phosphine oxide or other degradation product. The phosphine should have sufficient stability to remain as a phosphine and remain bound to the Re via a phosphorus-rhenium coordination bond. Thus, generally, at least one of $R^d$, $R^e$, and $R^f$ is aromatic (e.g., phenyl) or an alkyl group having hydroxy or ether groups. More typically, $R^d$, $R^e$, and $R^f$ are not alkyl groups composed of only carbon and hydrogen, since such phosphines are typically substantially reactive with air and water.

In some embodiments, none of $R^d$, $R^e$, and $R^f$ contains a phosphorus atom. In that case, the phosphine molecule according to Formula (7) contains only one phosphorus atom and is a mono-phosphine. Some examples of mono-phosphine molecules include triphenylphosphine, tris-(o-tolyl)phosphine, tris-(p-tolyl)phosphine, tris-(o-methoxyphenyl)phosphine, tris-(m-methoxyphenyl)phosphine, tris-(p-methoxyphenyl)phosphine, and tris(hydroxymethyl)phosphine. In other embodiments, one of $R^d$, $R^e$, and $R^f$ contains a phosphorus atom attached to hydrocarbon groups with the same type of structure provided in Formula (7) above. In that case, the phosphine molecule according to Formula (7) includes two phosphorus atoms and is a diphosphine. The diphosphine will generally bind to the rhenium(I) as a bidentate ligand, in which case only a single L group remains available as, for example, CO, a different phosphine, or a solvent molecule. Some examples of diphosphine molecules include 2,2'-bis(diphenylphosphino)-1,1'-biphenyl, 2,2'-bis(dicyclohexylphosphino)-1,1'-biphenyl, ethylenebis(diphenylphosphine), 2,2'-bis[di(3,5-di-t-butylphenyl)phosphino]-6,6'-dimethoxy-1,1'-biphenyl, 2,2'-bis[bis(4-methoxy-3,5-di-t-butylphenyl)phosphino]-4,4',6,6'-tetramethoxy-1,1'-biphenyl, 2,2'-bis(diphenylphosphino)-1,1'-binaphthyl (BINAP), 2,2'-bis(diphenylphosphino)-6,6'-dimethoxy-1,1'-biphenyl, and 1,2-bis[(2-methoxyphenyl)(phenyl)phosphino]ethane.

In some embodiments, two of $R^d$, $R^e$, and $R^f$ interconnect to form a phosphorus-containing ring. The interconnection typically includes carbon-carbon unsaturated bonds, e.g., a phosphabenzene (i.e., phosphorine or phosphinine), a phosphole, or phosphaphenalene. In other embodiments, all three of $R^d$, $R^e$, and $R^f$ interconnect to form a phosphorus-containing bicyclic or higher multicyclic (e.g., adamantane) structure. In each case, the resulting phosphine contains a phosphorus atom as a ring phosphorus atom. Generally, the phosphorus-containing ring contains one or more heteroatoms other than phosphorus, e.g., ether or tertiary amine groups within the ring. Some examples of such cyclic phosphines include 1,3,5-triaza-7-phosphaadamantane (PTA) and 3,7-diacetyl-1,3,7-triaza-5-phosphabicyclo[3.3.1]nonane (DAPTA). PTA and DAPTA phosphine molecules are described in, for example, D. J. Darensbourg, et al., *Organometallics,* 2004, 23 (8), pp 1747-1754, the contents of which are herein incorporated by reference in their entirety. In some embodiments, none of $R^d$, $R^e$, and $R^f$ interconnect to form a phosphorus-containing ring. In that case, the phosphine ligand does not contains a phosphorus atom as a ring phosphorus atom.

Some particular examples of phosphine ligands include the following:

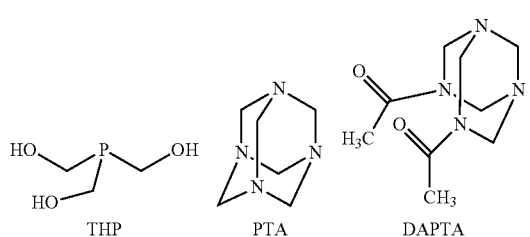

THP   PTA   DAPTA

The solvent molecules considered herein as one or more L groups are neutral (uncharged) molecules that typically have melting (freezing) points of up to or less than 40, 35, 30, 25, 20, 10, or 0° C. The solvent molecule may be selected from, for example, water ($H_2O$), alcohols (ROH, where scope of R has been provided above), ethers (ROR), amides ($R_2NC(O)R$, where one or more R groups may alternatively be hydrogen atoms), sulfoxides (RS(O)R), nitriles (RCN), and ketones (RC(O)R), wherein multiple R groups in a solvent molecule are independently selected (i.e., may be the same or different) and may or may not interconnect to form a ring. Some examples of alcohol solvents include methanol, ethanol, n-propanol, isopropanol, n-butanol, isobutanol, and phenol; some examples of ether solvents include diethyl ether, tetrahydrofuran, and dimethoxyethane (glyme); some examples of amide solvents include formamide, dimethylformamide, dimethylacetamide, dimethylpropionamide, and N-methylpyrrolidinone; an example of a sulfoxide solvent includes dimethylsulfoxide; some examples of nitrile solvents include acetonitrile and propionitrile; some examples of ketone solvents include acetone, 2-butanone, 2-pentanone, 3-pentanone, and cyclohexanone. For purposes of the invention, the solvent does not include amines (i.e., of the formula $NR^1R^2R^3$), phosphines (i.e., of the formula $PR^5R^6R^7$) or acid compounds. Numerous other solvents, including some that are not easily classified, are considered herein, such as hexamethylphosphoramide (HMPA).

The non-coordinating monovalent anion $X^-$ in Formula (1) can be any such anions well-known in the art, provided that the anion is safe for internal administration. Some examples of the anion $X^-$ include $SO_3CF_3^-$ (i.e., OTf), $PF_6^-$, tosylate, $SbF_6^-$, borate anions, $AsF_6^-$, $ClO_4^-$, and carborane anions.

The rhenium complexes described herein can be synthesized according to methodologies and techniques well known in the art. In a typical synthesis, a precursor rhenium carbonyl complex, e.g., $Re(CO)_5Cl$, as described in S. C. Marker et al., *Inorg. Chem.* 2018, 57, 1311-1331, is reacted with a bidentate ligand, as described above, under conditions in which two of the CO molecules are replaced with the bidentate ligand. For example, $Re(CO)_5Cl$ can be reacted with the bidentate ligand dmphen, as depicted earlier above, to produce $Re(CO)_3(dmphen)Cl$. The synthetic details for producing $Re(CO)_3(dmphen)Cl$ can be found in, for example, P. Kurz, et al., *Eur. J. Inorg. Chem.* 2006, 2966-2974 and J. M. Smieja, et al., *Inorg. Chem.* 2010, 49, 9283-9289. For purposes of the present invention, the latter complex can then be reacted with an isonitrile ligand (CNR) under suitable conditions to result in binding of the isonitrile ligand to the Re, thereby resulting in a $Re(CO)_3(dmphen)$ (CNR) complex. A wide variety of isonitrile ligands can be produced by known methods. For example, p-tolyl-isonitrile may be synthesized from p-tolyl-formamide using the experimental procedure described in, for example, Y. Yuan, et al., *J. Org. Chem.* 2018, 83, 2840-2846. To include the anion ($X^-$), the complex may first be chlorinated to produce an intermediate rhenium chloride, and the chlorine replaced with a neutral molecule and $X^-$ by reaction with the corresponding AgX salt. See, for example, A. E. Pierri et al., *J. Am. Chem. Soc.*, 134, pp. 18197-18200, 2012, the contents of which are herein incorporated by reference in their entirety.

In another aspect, the invention is directed to pharmaceutical compositions that contain any of the above-described rhenium(I) complexes dispersed in a pharmaceutically acceptable carrier, i.e., vehicle or excipient. The complex is dispersed in the pharmaceutically acceptable carrier by either being mixed (e.g., in solid form with a solid carrier) or dissolved or emulsified in a liquid carrier. The pharmaceutical composition may or may not also be formulated together with one or more additional active ingredients or adjuvants that improve the overall efficacy of the pharmaceutical composition, particularly as relates to the treatment of cancer.

The rhenium(I) complex and carrier may be formulated into pharmaceutical compositions and dosage forms according to methods well known in the art. The pharmaceutical compositions of the present invention may be specially formulated for administration in liquid or solid form. However, as the complexes described herein are particularly suited for injection, liquid formulations suitable for injection are particularly considered herein. Nevertheless, the pharmaceutical formulation may be formulated for oral administration (e.g., as tablets, capsules, powders, granules, pastes, solutions, suspensions, drenches, or syrups); parenteral administration (e.g., by subcutaneous, intramuscular or intravenous injection as provided by, for example, a sterile solution or suspension); topical application (e.g., as a cream, ointment, or spray); intravaginal or intrarectal administration (e.g., as a pessary, cream or foam); sublingual or buccal administration; ocular administration; transdermal administration; or nasal administration.

The phrase "pharmaceutically acceptable" refers herein to those compounds, materials, compositions, and/or dosage forms which are, within the scope of sound medical judgment, suitable for administration to a subject. The phrase "pharmaceutically acceptable carrier," as used herein, refers to a pharmaceutically-acceptable vehicle, such as a liquid or solid filler, diluent, carrier, manufacturing aid (e.g., lubricant, talc magnesium, calcium or zinc stearate, or stearic acid), solvent, or encapsulating material, that serves to carry the therapeutic composition for administration to the subject. Each carrier should be "acceptable" in the sense of being compatible with the other ingredients of the formulation and physiologically safe to the subject. Any of the carriers known in the art can be suitable herein depending on the mode of administration.

Some examples of materials that can serve as pharmaceutically-acceptable excipients, particularly for liquid forms, include water; isotonic saline; pH buffering agents; sugars (e.g., lactose, glucose, sucrose, and oligosaccharides, such as sucrose, trehalose, lactose, or dextran); and antimicrobials. Other excipients, more typically used in solid dosage forms, may also be included, e.g., starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

In some embodiments, the carrier further includes a molecular or microscopic (e.g., microscale or nanoscale) sub-carrier in which the complex is loaded, either within and/or conjugated onto the surface of the sub-carrier. The sub-carrier can be composed of, for example, a biocompatible and biodegradable polymer, e.g., based on a polyhydroxyacid biopolyester or polysaccharide. The overall structure of the sub-carrier can be, a micelle, a liposome, dendrimer, nanoparticle, or porous scaffold. These and numerous other types of sub-carriers are well known in the art. The sub-carrier may function to protect the complex during transit, e.g., while in the bloodstream or while passing through the gastrointestinal tract, to release the complex closer to the target cells with lower chance of degradation. The sub-carrier may also be functionalized with one or more targeting agents that selectively target a class of cells to be treated with the complex. In particular embodiments, the targeting agent selectively targets cancer cells or specific types of cancer cells. The targeting agent can be, for example, an antibody, antibody fragment, or small molecule receptor binder.

In another aspect, the invention is directed to a method for treating a condition (e.g., disease or disorder) in which inducing endoplasmic reticulum (ER) stress is beneficial (i.e., results in a beneficial outcome, such as mitigation or reversal of the condition). The method achieves this by administering any of the rhenium(I) complexes in a pharmaceutically effective amount to a patient having any such condition. The term "beneficial" or "beneficial outcome," as used herein, refers to a reduction, mitigation, or prevention of signs and/or symptoms associated with the condition. In particular embodiments, the condition being treated is a cancer. A beneficial outcome in treating the cancer may refer to, for example, an inhibition or reduction in the growth of a tumor, or a reduction in the size of a tumor, or a prevention of tumor formation or growth from pre-cancerous tissue (i.e., prevention of pre-cancerous tissue turning into cancerous tissue).

The ER is a major regulator of, inter alia, cancer cell proliferation, metastasis, angiogenesis, and chemotherapy resistance. Cancer cells often exhibit higher rates of protein synthesis than non-cancer cells, which raises their ER protein load and leads to higher basal levels of ER stress (Y. -P. Vandewynckel, et al., *Anticancer Res.* 2013, 33, 4683-4694). To handle this ER stress, cancer cells often employ the unfolded protein response (UPR). The UPR is typically cytoprotective, and its increased activation in cancer cells can cause them to be more virulent and more resistant to chemotherapy (M. J. Mann, et al., *Cancer Biol. Ther.* 2006, 5, 736-740). However, acute inductions of high levels of ER stress can shift the UPR to activate apoptosis (R. Sano et al., *Biochim. Biophys. Acta—Mol. Cell Res.* 2013, 1833, 3460-3470). The higher basal ER stress levels of cancer cells makes them more susceptible than normal cells to apoptosis induction via overactivation of the UPR. Thus, the use of the rhenium(I) complexes described herein, which operate by induction of ER stress, represents a novel strategy for the treatment of cancer.

In the method, any of the above described rhenium(I) complexes, typically as a pharmaceutical formulation, is administered to the subject in a pharmaceutically effective amount to treat a disease or condition, such as a cancer, that benefits from induction of ER stress. The mode of administration may be any of the modes of administration used for the platinum-based drugs, such as cisplatin. The typical mode of administration for purposes of the present invention is by intravenous injection. In one embodiment, the complex is injected into the bloodstream, in which case the complex is systemically distributed through the body. In another embodiment, the complex is injected locally directly into or in the vicinity of cancerous tissue.

The cancer can be any of a wide varieties of cancer, particularly those cancers for which platinum drugs are known to be useful. The claimed rhenium(I) complexes can be used as a replacement of platinum drugs for treating any such cancers, and particularly those cancers found to be or having a tendency to be resistant to platinum-based treatment. In particular embodiments, the cancer being treated is ovarian cancer, testicular cancer, prostate cancer, cervical cancer, breast cancer (e.g., triple negative breast cancer), lung cancer, mesothelioma, squamous cell cancer, colon cancer, gastrointestinal cancer, stomach cancer, pancreatic cancer, bladder cancer, esophageal cancer, head-and-neck cancer, skin cancer, brain cancer, diffuse large cell lymphoma, lymphatic cancer, follicular B cell lymphoma, lymphocytic leukemia, multiple myeloma, Burkitt's lymphoma, primary mediastinal B-cell lymphoma, Hodgkin's lymphoma, non-Hodgkin's lymphoma, mantle cell lymphoma, Kaposi's sarcoma, and Cowden's syndrome. In some embodiments, the cancer is characterized by a multidrug resistant (MDR) tumor.

In particular embodiments, the cancer being treated is ovarian cancer, particularly epithelial ovarian cancer. Epithelial ovarian cancer is the most lethal form of gynecological cancers, claiming the lives of over 100,000 women annually. Despite significant breakthroughs in the field of oncology, the average survival rate of patients diagnosed with epithelial ovarian cancer has remained stagnant during the last 30 years (S. Vaughn et al., *Nat. Rev. Cancer* 2011, 11, 719-725). This stagnation reflects both the lack of new clinical treatment options and the limitations of existing drugs.

The most widely used chemotherapeutic agents for ovarian cancer are the platinum-based drugs cisplatin and carboplatin. These platinum coordination compounds are cytotoxic drugs that kill cancer cells by forming covalent intrastrand crosslinks with genomic DNA (Jamieson, E. R., et al., *Chem. Rev.* 1999, 99, 2467-2498). The resulting Pt-DNA adducts sufficiently distort the double helical structure of DNA to inhibit transcription and trigger apoptosis (Jung, Y. et al., *Chem. Rev.* 2007, 107, 1387-1407). Although these drugs are employed as part of the first-line therapeutic treatment of ovarian cancer, the poor patient survival rate for this condition is a clear indication that improvements are critically needed. Platinum-based drugs have several key limitations, including the following: (1) because of their indiscriminate DNA-binding properties, these complexes induce a wide range of toxic side effects, which degrade patient quality of life (Hartmann, J. T., et al., *Expert Opin. Pharmacother.* 2003, 4, 889-901). These off-target side effects decrease the therapeutic window of these compounds, preventing the administration of doses required for complete cancer remission. (2) In the case of tumor relapse, an occurrence in 70% of all ovarian cancer patients, the cancer often returns in a form that is resistant or non-responsive to platinum chemotherapy. Thus, cisplatin and carboplatin are substantially less effective for relapsed ovarian cancer (Markman, M., et al., *Oncologist* 2000, 5, 26-35) a factor that contributes to the high mortality rate of these patients. (3) The currently available platinum drugs do not possess spectroscopic or nuclear properties that are suitable for in vitro or in vivo imaging (Cheff, D. M. et al., *J. Med. Chem.* 2017, 60, 4517-4532). Imaging modalities would facilitate the assessment of patient response to these drugs and guide clinicians on dosing strategies.

Recent efforts have focused on the development of molecularly targeted agents for the treatment of relapsed ovarian cancer. These therapies, however, rely on specific cancer genotypes to be effective. For example, the recently approved PARP inhibitors olparib and rucaparib are only effective in ovarian cancer patients with BRCA gene mutations, a population that represents approximately only 20% of all patients (Lord, C. J. et al., *Curr. Opin. Pharmacol.* 2008, 8, 363-369; Pan, Z. et al., *Oncotarget* 2017, 8, 97657-97670). These targeted therapy strategies, therefore, are not broadly effective in all ovarian cancer patients. The development of new cytotoxic drugs with novel targets and mechanisms of action will be a crucial component for prolonging patient survival. Significantly, the novel class of rhenium(I) cytotoxic drugs described herein overcome the major limitations of the platinum-based drugs in relapsed ovarian cancer.

Targeting the ER of ovarian cancer and the induction of the UPR is a highly promising therapeutic strategy (Nagelkerke, A. et al., *Biochim. Biophys. Acta—Rev. Cancer* 2014, 1846, 277-284; Wang, M. et al., *Crit. Rev. Oncol. Hematol.* 2018, 127, 66-79) that has only been clinically realized by the proteasome inhibitors bortezomib and carfilzomib (Obeng, E. A. et al., *Blood* 2006, 107, 4907-4916). Furthermore, ovarian cancer cells overexpress GRP78 (Delie, F. et al., *J. Oncol.* 2012, 2012, Article ID 468615) a protein that mediates ER stress via the UPR (Pfaffenbach, K. T. et al., *Curr. Opin. Cell Biol.* 2011, 23, 150-156). As a consequence of this distinct protein expression profile, ovarian cancer cells are more susceptible to cytotoxic agents that induce ER stress compared to non-cancer cells (Bastola, P. et al., *Mol. Oncol.* 2016, 10, 1559-1574). Based on the unique mechanism of action of the rhenium complexes described herein, they have the ability to selectively target ovarian cancer cells. Without being bound by any theory, it is believed that the application of a source of acute ER stress selectively overburdens the UPR of ovarian cancer cells, which causes a shift to the pro-apoptotic arm of the UPR (Schonthal, A. H., *Front. Biosci.* 2012, S4, 412-431). In the context of platinum-resistant ovarian cancer, chronic treatment with cisplatin gives rise to higher expression levels of GRP78, and likewise the malignancy status of ovarian cancer is correlated with GRP78 expression levels (Chen, T. et al., Chronic Exposure of Cisplatin Induces GRP78 Expression in Ovarian Cancer. In Proceedings of the 2017 4th International Conference on Biomedical and Bioinformatics Engineering—ICBBE 2017; ACM Press: New York, New York, USA, 2017; pp 35-38; Huang, L. W. et al., Overexpression of GRP78 Is Associated with Malignant Transformation in Epithelial Ovarian Tumors. *Appl. Immunohistochem. Mol. Morphol.* 2012, 20, 381-385). Thus, higher basal levels of ER stress exist in these resistant forms of ovarian cancer, reflecting their increased sensitivity to acute ER stress. The use of these ER stress-inducing rhenium complexes provides an opportunity for the selective treatment of platinum-resistant ovarian cancer.

In the treatment, the rhenium complex is administered in a therapeutically effective amount. The effective amount of the compound to be administered can be readily determined according to methods familiar to physicians and clinicians, e.g., during pre-clinical and clinical trials. As is well known in the art, the dosage of the active ingredient(s) depends on such factors as the type and stage of the condition, such as cancer, the method of administration, size of the patient, and potential side effects. Dosing is dependent on the severity and responsiveness of the cancer being treated, with the course of treatment lasting from several days to several months, or until a cure is effected or a diminution of the disease state is achieved. Optimal dosing schedules can be calculated from measurements of drug accumulation in the body of the patient. The administering physician can determine optimum dosages, dosing methodologies, and repetition rates. In different embodiments, depending on these and other factors, a suitable dosage of the active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, per 50 kg, 60 kg, or 70 kg adult, or a dosage within a range bounded by any of the foregoing exemplary dosages. Depending on these and other factors, the composition is administered in the indicated dosage by any suitable schedule, e.g., once, twice, or three times a day for a total treatment time of one, two, three, four, or five days, and up to, for example, one, two, three, or four weeks or months. The indicated dosage may alternatively be administered every two or three days, or per week. Alternatively, or in addition, the composition is administered until a desired change is evidenced.

Any of the rhenium complexes described above may (i.e., optionally) be co-administered with one or more other therapeutic agents outside the scope of Formula (1). In a first instance, the co-administration is accomplished by including the complex of Formula (1) in admixture with one or more other therapeutic agents in the same pharmaceutical composition being administered. In a second instance, the co-administration can be accomplished by administering the complex of Formula (1) separately from one or more other therapeutic agents, i.e., at the same time or at different times. In particular, an additional antineoplastic (e.g., anticancer drug or adjuvant) agent may or may not be included in the treatment. Anticancer agents or adjuvants suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, inhibit protein kinase activity, block receptors for growth factors, cytokines, activating ligands, and the like. In some embodiments, the rhenium complex is administered as the sole anticancer drug.

In particular embodiments, the rhenium complex is co-administered with a compound that inhibits dephosphorylation of the master regulatory protein eukaryotic initiation factor $2\alpha$ (eIF$2\alpha$). In some embodiments, the combination treatment results in a synergistic effect in treating cancer. The synergistic effect suggests that the activity of the rhenium complexes is related to the phosphorylation of eIF$2\alpha$. A particular example of an eIF$2\alpha$ inhibitor includes salubrinal and its analogues and derivatives. The eIF$2\alpha$ selective inhibiting ability of salubrinal, in particular, is discussed in, for example, Boyce, M. et al., A Selective Inhibitor of EIF$2\alpha$ Dephosphorylation Protects Cells from ER Stress. *Science* 2005, 307, 935-939.

The Re(I) complexes described herein are advantageously significantly cytotoxic to cancer cells while eliciting minimal or substantially no toxic side effects to normal tissue. As well known in the art, the cytotoxicity of a given drug can be expressed as an IC$_{50}$ value. Depending on the precise structure of the complex and the type of cancer being treated, the complexes described herein can exhibit an IC$_{50}$ value of up to or less than 20, 15, 10, 5, 4, 3, 2, or 1 µM. The complexes described herein are further advantageous by being detectable or imageable by virtue of the inherent luminescence possessed by the rhenium(I) ion. In some embodiments, fluorescence or magnetic resonance imaging is used for imaging the distribution of rhenium in bodily tissue or to track the intracellular localization. In other embodiments, the complexes can be observed by vibrational microscopy at vibrational energies in resonance with infrared transitions in the CO ligands. Another significant advantage of the complexes described herein is their insusceptibility to resistance mechanisms, unlike the platinum-based drugs.

Examples have been set forth below for the purpose of illustration and to describe the best mode of the invention at the present time. However, the scope of this invention is not to be in any way limited by the examples set forth herein.

EXAMPLES

Synthesis of $[Re(CO)_3(dmphen)(p\text{-}tol\text{-}ICN)]Cl$ (TRIP)

The following experiments are primarily directed to the study of a new rhenium(I) tricarbonyl complex (TRIP), which bears a chelating polypyridyl ligand and an axial isonitrile ligand as a potent anticancer agent. The structure of TRIP is provided in FIG. 1. As further discussed below, the evidence reveals that TRIP, in particular, is an effective ER stress-inducing agent with significant antiproliferative activity.

TRIP was synthesized by treating the previously reported complex $[Re(CO)_3(dmphen)OTf]$ with excess 4-methylphenyl isonitrile in tetrahydrofuran. TRIP was fully characterized using $^1H$ NMR and IR spectroscopy, HR-MS, and X-ray diffraction. The purity of the complex was verified via elemental analysis and HPLC. The water-soluble complex is luminescent upon irradiation with UVA and blue light and exhibits a luminescence quantum yield of 3% and a lifetime of 1.05 μs in aqueous, air-equilibrated phosphate buffer. The complex is stable indefinitely as a solid and in aqueous solution for over one week. TRIP is also stable in the presence of millimolar concentrations of glutathione. Based on TRIP's favorable physical properties and high stability, TRIP was evaluated for its potential as an anticancer agent in vitro.

TRIP was synthesized as follows: $Re(CO)_3(dmphen)Cl$ (0.266 g, 0.52 mmol) is dissolved in THF and AgOTf (0.133 g, 0.52 mmol) is added. The mixture is heated at reflux for 3 h, after which the resulting yellow suspension is filtered. To the filtrate, p-tolyl-isonitrile (0.2 g, 1.7 mmol) is added, and the mixture is heated at reflux overnight. The resulting orange solution is evaporated to dryness, and the residue is dissolved in a minimum amount of methanol ($\approx$5 mL). Saturated ammonium hexafluorophosphate (5 mL) is added, and the resulting suspension is filtered after 10 min. The pale yellow solid product is washed with diethyl ether and is recrystallized by slow addition of water to a saturated methanolic solution. The pure solid, as a $PF_6^-$ salt, is then dissolved in acetonitrile (15 mL) and stirred with IRA-410 (Cl) anion exchange resin ($\approx$5 g) overnight. The mixture is filtered, and the resin is washed with acetonitrile (10 mL). The combined acetonitrile filtrate is then evaporated to dryness to yield the product as a pale yellow solid. Yield: 61%. $^1H$ NMR (400 MHz, $D_2O$) δ 8.56 (d, J=8.6 Hz, 2H), 8.00 (s, 2H), 7.94 (d, J=8.4 Hz, 2H), 7.06 (d, J=7.3 Hz, 2H), 6.84 (d, J=9.0 Hz, 2H), 3.28 (s, 6H), 2.21 (s, 3H). IR (KBr, $cm^{-1}$): 2176 m, 2040 s, 1946 s, 1923 s. HR-ESI-MS (positive ion mode): m/z 596.095 ($[M]^+$, calcd 596.098). Anal. Calcd for $[Re(CO)_3(dmphen)(p\text{-}tol\text{-}ICN)]Cl \cdot 2.5H_2O$ ($ReC_{25}H_{24}N_3O_{5.5}Cl$): C, 44.41; H, 3.58; N, 6.20. Found: C, 44.02; H, 3.71; N, 6.21.

Cytotoxicity Experiments on TRIP

HeLa (cervical cancer) and A549 (lung cancer) cell lines were obtained from American Type Culture Collection (ATCC) and cultured using Dulbecco's Modified Eagle's Medium (DMEM) supplemented with 10% fetal bovine serum (FBS). A2780 (ovarian cancer) and A2780CP70 (cisplatin-resistant ovarian cancer) cell lines were provided by the Cell Culture Facility of Fox Chase Cancer Center (Philadelphia, PA). These cells were cultured as monolayers with Roswell Park Memorial Institute (RPMI)-1640 culture media supplemented with 10% FBS. HEK295 (healthy kidney) cell line was obtained from ATCC and cultured using Modified Eagle's Medium (MEM) supplemented with 10% FBS. Knock-in loss-of-function eIF2α mutant (eIF2α, A/A) and isogenic wild-type (eIF2α, S/S) MEF cells were supplied by Dr. Randal Kaufman (Sanford-Burnham Medical Research Institute, La Jolla, CA, USA). Wild-type (S/S) and eIF2α(A/A) MEFs were cultured in DMEM, pH 7.4, containing 1 mM pyruvate and 4 mM glutamine and supplemented with 1× non-essential amino acid mix (Gibco/Invitrogen), 100 units/mL penicillin and 100 μg/mL streptomycin (pen/strep; Gibco/Invitrogen) and 10% FBS. All cell lines were grown in a humidified incubator at 37° C. with an atmosphere of 5% $CO_2$. Cells were passed at 80-90% confluence using trypsin/EDTA. Cells were tested monthly for *mycoplasma* contamination with the PlasmoTest™ *mycoplasma* detection kit from InvivoGen.

All compounds were dissolved in PBS at pH 7.4 to prepare 1-2 mM stock solutions. For cell viability studies, all cells were grown to 80-90% confluence, detached with trypsin/EDTA, seeded in 96-well plates at 4000-8000 cells/well in 100 μL of growth media, and incubated for 24 hours. The medium was removed and replaced with fresh medium (200 μL) containing varying dilutions of either the rhenium compounds, cisplatin, or media. The cells were then incubated for 48 hours. The medium was removed from the wells, and 3-(4,5-dimethylthiazol-2-yl)-2,5-tetrazolium bromide (MTT) in DMEM, RPMI, or MEM (200 μL, 1 mg/mL) was added. The additional 48 hours incubation was performed to ensure that the cells were in the logarithmic growth phase and that the cells had adequate time to regrow after exposure to the complexes. After 4 hours, the MTT/DMEM, RPMI, or MEM solution was removed, and the formazan crystals were dissolved in 200 μL of an 8:1 mixture of DMSO and pH 10 glycine buffer. The absorbance at 570 nm in each well was measured using a BioTek Synergy HT plate reader. Cell viability was determined by normalizing the absorbance of the treated wells to untreated wells. The % viability data shown is an average of three independent experiments with six replicates per concentration The cytotoxicity of TRIP was investigated in a panel of cancer and non-cancer cell lines to determine its potential as a therapeutic agent. For comparison, the activities of the established metal-based anticancer drug cisplatin and another potent rhenium anticancer agent, $[Re(CO)_3(dmphen)(OH_2)]^+$ (Neo-Re), were evaluated (e.g., K. M. Knopf et al. *J. Am. Chem. Soc.* 2017, 139, 14302-14314). The concentrations of these complexes required to reduce cell viability to 50% of the control ($IC_{50}$) are shown in Table 1 below. In comparison to cisplatin and Neo-Re, TRIP was found to have comparable or greater toxicity in all cancer cell lines tested. Based on its promising anticancer activity, TRIP was submitted for screening in the National Cancer Institute (NCI)-60 cell line panel. The results indicate that TRIP is most potent in melanoma and breast cancer cells lines and least effective in lung and renal cancer cell lines. The activity of TRIP in this cell line panel was compared to drugs in the NCI database via the COMPARE algorithm, which compares the toxicity profiles of drugs to reveal correlations in their activity (D. W. Zaharevitz et al., *J. Mol. Graph. Model.* 2002, 20, 297-303). Highest correlations were observed for DNA-binding agents chromomycin A3 and actinomycin D and the translation inhibitors pyllanthoside, bruceantin, and didemnin B. Notably, the spectrum of activity of TRIP was not correlated to any of the platinum-based drugs, and it exhibits only a moderate correlation (PCC=0.403) to Neo-Re. The high correlations to established transcription and translation inhibitors indicates that TRIP may act similarly.

TABLE 1

$IC_{50}$ values of TRIP, Neo-Re, and cisplatin in cancer and non-cancer cell lines.

| Compound | $IC_{50}$ (μM) | | | | |
|---|---|---|---|---|---|
| | A2780 (ovarian cancer) | A2780 CP70 (cisplatin-resistant ovarian cancer) | HeLa (cervical cancer) | A549 (lung cancer) | HEK293 (kidney) |
| TRIP | 1.7 ± 0.7 | 1.9 ± 1 | 1.4 ± 0.2 | 1.4 ± 0.6 | 1.9 ± 0.2 |
| Neo-Re | 5.7 ± 0.6 | 6.0 ± 0.2 | 4.4 ± 1.3 | 7.7 ± 2.4 | 9.0 ± 0.3 |
| Cisplatin | 1.3 ± 0.1 | 12 ± 3 | 6.6 ± 0.7 | 5.6 ± 0.5 | 1.7 ± 0.2 |

To determine the type of cell death induced by TRIP, the cytotoxicity of this compound in A2780 cells was evaluated in the presence of inhibitors of various established cell death pathways. Inhibitors of necroptosis, paraptosis, and ferroptosis did not alter TRIP's activity, but the pan-caspase inhibitor Z-VAD-FMK significantly decreased TRIP's cytotoxicity. Because the activation of caspases is often critical for the execution of apoptosis, this result indicates that TRIP may be inducing apoptosis. To confirm that TRIP induces caspase-dependent apoptosis, western blots were first performed to detect apoptosis markers caspase 3 and cleaved PARP. The cell death pathway was further verified by performing the annexin V assay, which selectively stains apoptotic cells. To determine whether TRIP induced apoptosis by the intrinsic pathway, the release of cytochrome c from the mitochondria was tracked using flow cytometry. Cytochrome c release occurs on the same time scale as apoptosis induction by TRIP, indicating that TRIP induces intrinsic apoptosis.

Figure 2:
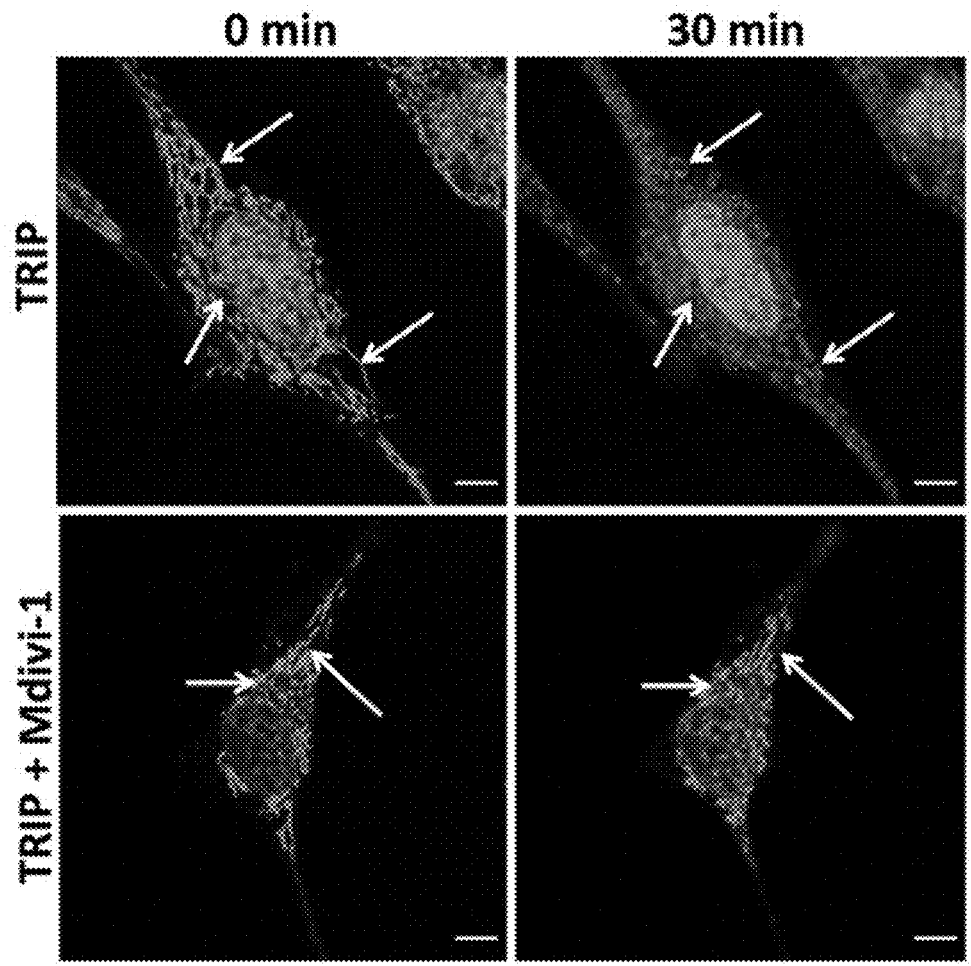
FIG. 2 shows HeLa cells stained with MitoTracker Red and Hoechst dye treated with TRIP (5 μM) for 0 and 30 minutes (left and right top panels, respectively).

Given the promising activity of TRIP in a variety of cancer cell lines and its ability to induce intrinsic apoptosis, its intracellular localization and early cellular effects were explored. The localization of TRIP was probed by measuring the colocalization of TRIP luminescence with organelle-specific fluorescent small molecules or fusion proteins. Partial colocalization was observed with the LysoTracker Red dye and GalT-dsRed fusion protein, but the majority of TRIP luminescence was cytosolic. While performing these colocalization studies, the observation was made that the mitochondrial morphology was noticeably altered in TRIP-treated cells. The mitochondria were significantly rounded and punctate after TRIP treatment, in contrast to the tubular, elongated morphology within untreated cells. Time-lapse microscopy experiments revealed that TRIP induces these changes after only 30 minutes of treatment in HeLa cells, as shown in FIG. 2. Although TRIP-treated mitochondria were visually different, mitochondrial polarization experiments with the ratiometric sensor JC-1 indicated that the mitochondria remained functional, demonstrating that the observed changes might be controlled mitochondrial fission rather than fragmentation. These morphology changes were curtailed in the presence of Mdivi-1, which inhibits dynamin-related protein 1 (Drp1), an essential mediator of fission, confirming that this process is due to mitochondrial fission (FIG. 2) (A. Cassidy-Stone et al., *Dev. Cell* 2008, 14, 193-204). Because mitochondrial fission is often associated with autophagy, the expression of LC3, an autophagosome marker, was examined in A2780 cells upon treatment with TRIP. After 24 hours, a large increase in LC3II expression relative to LC3I was observed in cells treated with TRIP. Based on these results, it is clear that TRIP induces both autophagy and apoptosis. Because TRIP does not depolarize the mitochondria or cause release of cytochrome c on short time scales, it is possible that a different organelle, such as the ER, may be the key target of this compound.

Figure 3A:
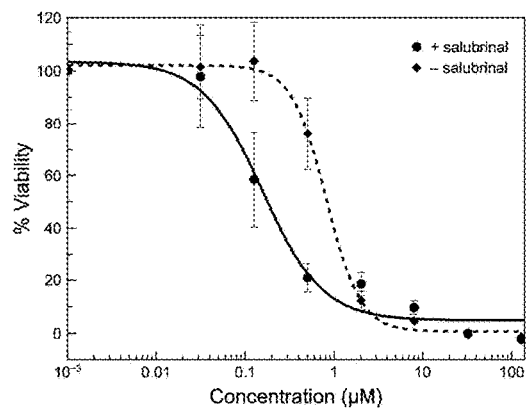
FIGS. 3A-3D show the following.
Figure 3B:
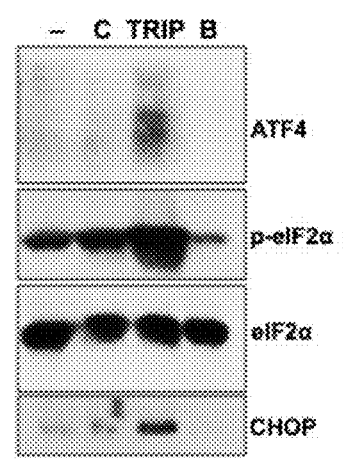
Figure 3C:
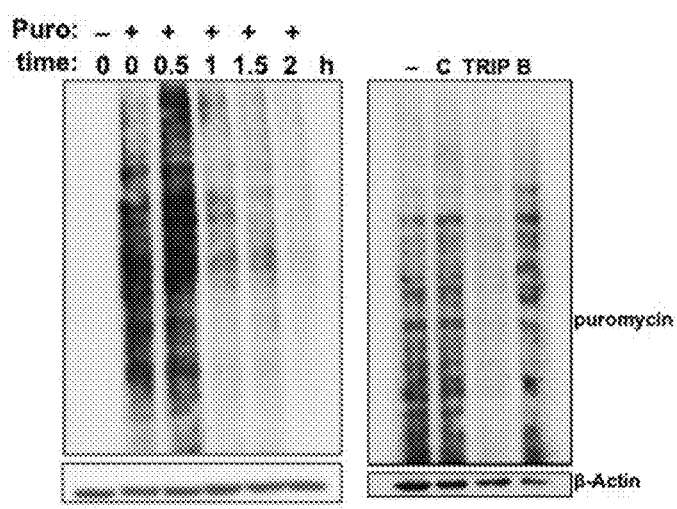

Because of the potential connections between mitochondrial fission, autophagy, and ER stress, the effects of the ER stress modulator salubrinal on the cytotoxicity of TRIP in A2780 cells were explored. Salubrinal operates by inhibiting dephosphorylation of the master regulatory protein eukaryotic initiation factor 2α (eIF2α), an integral component of the UPR. As shown by the data in FIG. 3A, the presence of salubrinal increases the activity of TRIP by a factor of 4. In view of this synergy, experiments were conducted to determine whether TRIP was acting to cause phosphorylation of eIF2α. As shown in FIG. 3B, Western blot analysis of A2780 cells treated with TRIP confirms the induction of eIF2α phosphorylation as little as 2 hours after exposure, which indicates that this process is one of the first cellular responses. Next, the downstream effects of eIF2α phosphorylation were investigated. The most immediate and pronounced effect of eIF2α phosphorylation is the inhibition of translation (S. R. Kimball, *Int. J. Biochem. Cell Biol.* 1999, 31, 25-29). To probe whether the levels of phosphorylation induced by TRIP were sufficient to inhibit protein translation, endogenous global translation levels were investigated using the puromycin incorporation assay (E. K. Schmidt et al., *Nat. Methods* 2009, 6, 275-277). As shown by the results in FIG. 3C, as early as 2 hour post incubation, A2780 cells treated with TRIP incorporated substantially less puromycin compared to the untreated controls, which indicates much lower rates of translation. The role of eIF2α in these processes was confirmed by testing TRIP in a mutant MEF cell line incapable of eIF2α phosphorylation. The mutant cells showed no changes in translation levels after TRIP treatment.

Hyperphosphorylation of eIF2α can lead to apoptosis via upregulation of the stress-related transcription factors ATF4 and CHOP (H. Matsumoto et al., *Biol. Open* 2013, 2, 1084-1090). The upregulation of these proteins was measured in response to TRIP treatment and it was observed that both ATF4 and CHOP were upregulated (FIG. 3B), linking the observed eIF2α phosphorylation and apoptosis. Phosphorylation of eIF2α also results in cell cycle arrest in the G1 phase (J. W. Brewer et al., *Proc. Natl. Acad. Sci. U.S.A.* 2000, 97, 12625-12630). Cells treated with TRIP showed an 18% increase in the population of cells in the G1 phase and a corresponding decrease in the number of cells in the S phase as opposed to untreated cells. Thus, the ability of TRIP to stall cells in the G1 phase is fully consistent with its induction of eIF2α phosphorylation. These results indicate that TRIP induces ER stress, triggering eIF2α phosphorylation and the resulting downstream effects, culminating in cellular apoptosis.

Figure 3D:
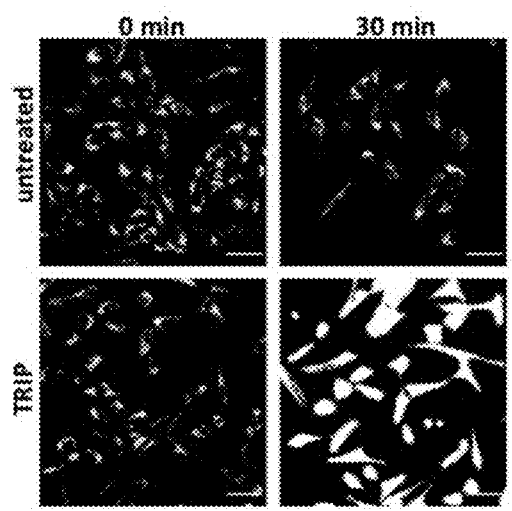

Phosphorylation of eIF2α often occurs due to the accumulation of misfolded proteins. To determine whether the observed phosphorylation was due to protein misfolding, the extent of misfolded protein accumulation induced by TRIP was evaluated using the dye Thioflavin T, (ThT) which fluoresces in the presence of protein aggregates (D. R. Beriault et al., *Biochim. Biophys. Acta—Mol. Cell Res.* 2013, 1833, 2293-2301). As shown by the results in FIG. 3D, the fluorescence intensity of ThT increased significantly in HeLa cells treated with TRIP in comparison to untreated cells within 30 minutes. Given the observation of fast protein aggregation upon treatment with TRIP, the induction of protein misfolding is most likely the cause of the ER stress and activation of the UPR.

Figure 4:
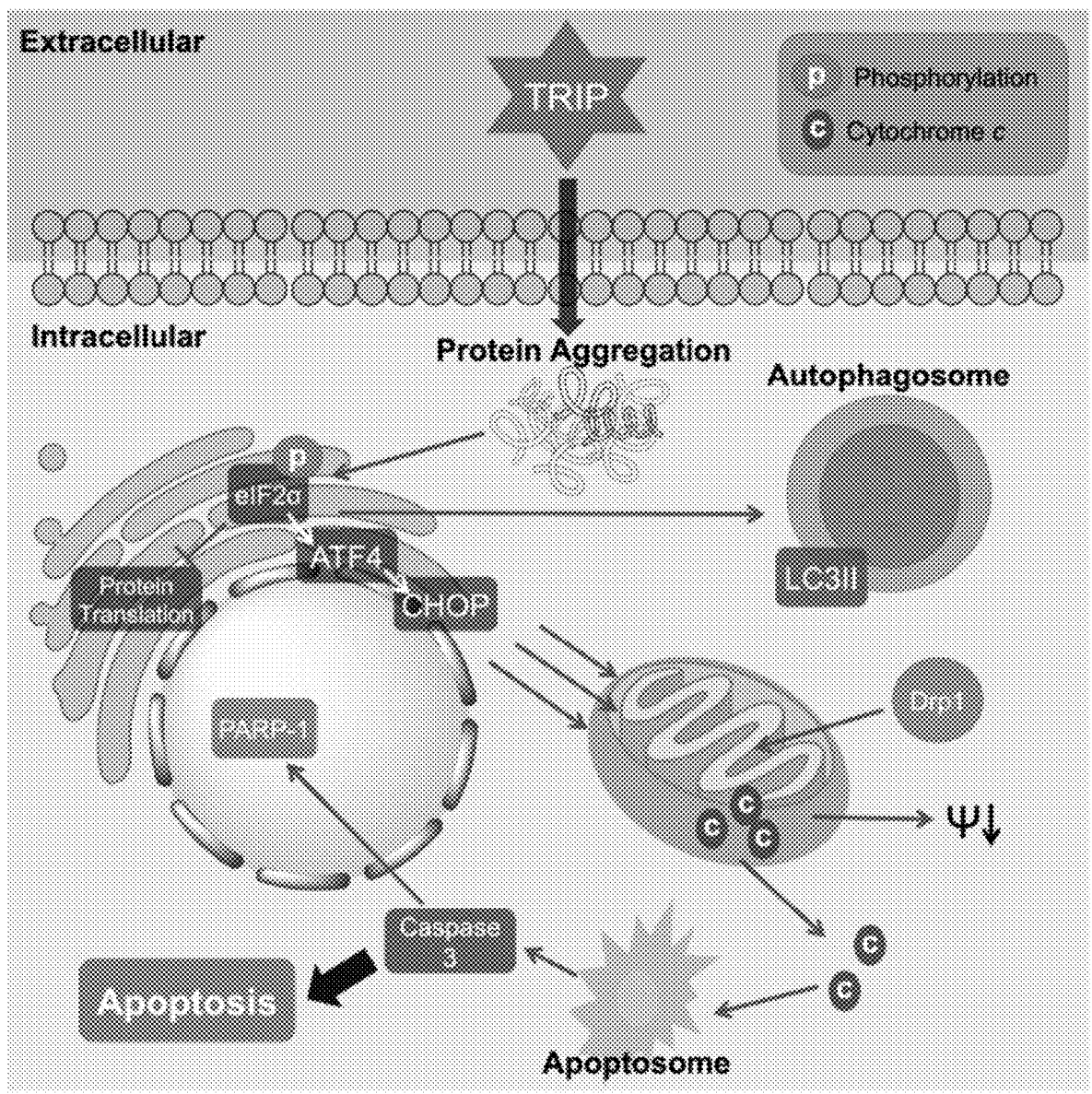
FIG. 4 shows a proposed mechanism of ER-stress and apoptosis induction by TRIP.

A summary of TRIP's mechanism of ER stress induction and the subsequent cellular response, as currently understood, is shown in FIG. 4. TRIP induces ER stress in less than 30 minutes after exposure due to the accumulation of misfolded proteins. Misfolded protein accumulation leads to the phosphorylation of eIF2α, which initiates autophagy, shuts down global protein translation, and upregulates ATF4. Prolonged eIF2α phosphorylation and upregulation of ATF4 leads to expression of the proapoptotic protein CHOP, which induces mitochondrial membrane depolarization and release of cytochrome c. Cytochrome c release then results in caspase activation and initiation of apoptosis. Although potential causes of eIF2α phosphorylation have been investigated, including proteasome inhibition, HSP90 inhibition, and reactive oxygen species generation, no evidence has been found that TRIP triggers protein misfolding via these pathways. A range of diverse metal complexes are known to induce ER stress. The major mechanism of action proposed for these agents is through the production of ROS. Only a few studies have discovered metal complexes that induce ER stress in the absence of ROS generation (e.g., M. J. Chow et al., *Chem. Sci.* 2016, 7, 4117-4124). Significantly, TRIP's ability to induce ER stress independent of ROS generation indicates that it operates via a different mechanism than many other metallodrugs targeting the ER. Collectively, these results establish TRIP and related rhenium(I) complexes containing an isonitrile ligand as promising anticancer agents that kill cells by causing the accumulation of misfolded proteins.

While there have been shown and described what are at present considered the preferred embodiments of the invention, those skilled in the art may make various changes and modifications which remain within the scope of the invention defined by the appended claims.

What is claimed is:

1. A composition comprising a rhenium(I) complex having the following structure:

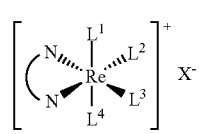

wherein

Re represents a rhenium ion having a +1 charge;

represents an uncharged bidentate ligand of one of the following structures

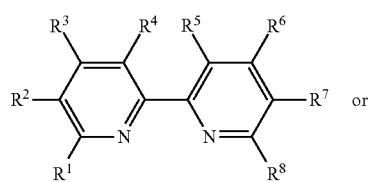

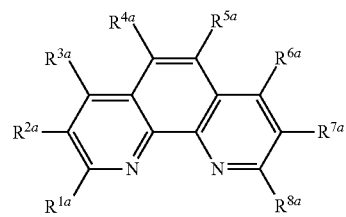

wherein $R^1$, $R^2$, $R^3$, $R^4$, $R^5$, $R^6$, $R^7$, $R^8$, $R^{1a}$, $R^{2a}$, $R^{3a}$, $R^{4a}$, $R^{5a}$, $R^{6a}$, $R^{7a}$, and $R^{8a}$ are each independently selected from the group consisting of hydrogen atoms; hydrocarbon groups (R') containing 1-6 carbon atoms; —OR$^a$ groups; —C(O)OR$^a$ groups; —OC(O)R$^a$ groups; —C(O)R$^a$ groups; and halogen atoms, wherein said hydrocarbon groups (R') optionally include one or more heteroatoms selected from oxygen, nitrogen, and sulfur, and R$^a$ is independently selected from hydrogen atoms and hydrocarbon groups (R'); and $L^1$ is an isonitrile ligand of the formula CN-R wherein R is an isonitrile ligand having the following structure:

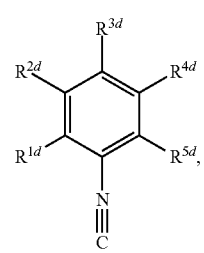

wherein $R^{1d}$ and $R^{5d}$ are hydrogen; and $R^{2d}$, $R^{3d}$, and $R^{4d}$ are independently selected from hydrogen atoms, hydrocarbon groups (R') containing 1-6 carbon atoms, —OR" groups, —C(O)OR" groups, —OC(O)R" groups, —C(O)R" groups, —NR"$_2$ groups, —C(O)NR"$_2$ groups, —NR"C(O)R" groups, halogen atoms, —CN groups, and nitro groups; wherein the hydrocarbon groups (R') optionally include one or more heteroatoms selected from oxygen, nitrogen, and sulfur; and R" is independently selected from hydrogen atoms and hydrocarbon groups (R');

$L^2$, $L^3$, and $L^4$ are each independently CO; and $X^{31}$ represents a non-coordinating monovalent anion.

2. The composition of claim 1, wherein

has the following structure:

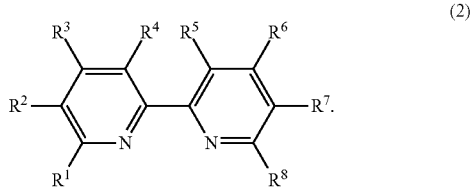

(2)

3. The composition of claim 2, wherein at least $R^3$ and $R^6$ and/or $R^1$ and $R^8$ are not hydrogen atoms.

4. The composition of claim 2, wherein at least two of $R^1$, $R^2$, $R^3$, $R^4$, $R^5$, $R^6$, $R^7$, and $R^8$ are independently selected from the group consisting of hydrocarbon groups (R') containing 1-6 carbon atoms; —$OR^a$ groups; —$C(O)OR^a$ groups; —$OC(O)R^a$ groups; and —$C(O)R^a$ groups.

5. The composition of claim 2, wherein at least one of $R^1$, $R^2$, $R^3$, and $R^4$ and at least one of $R^5$, $R^6$, $R^7$, and $R^8$ are each independently selected from the group consisting of hydrocarbon groups (R') containing 1-6 carbon atoms; —$OR^a$ groups; —$C(O)R^a$ groups; —$OC(O)R^a$ groups; and —$C(O)R^a$ groups.

6. The composition of claim 1, wherein

has the following structure:

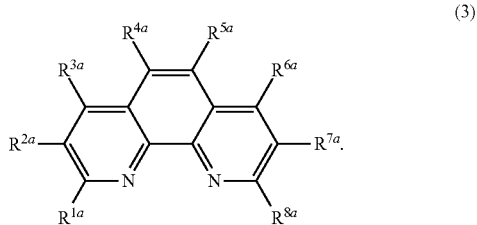

(3)

7. The composition of claim 6, wherein at least $R^{1a}$ and $R^{8a}$ and/or $R^{3a}$ and $R^{6a}$ are not hydrogen atoms.

8. The composition of claim 6, wherein at least one of $R^{1a}$, $R^{2a}$, $R^{3a}$, and $R^{4a}$ and at least one of $R^{5a}$, $R^{6a}$, $R^{7a}$, and $R^{8a}$ are each independently selected from the group consisting of hydrocarbon groups (R') containing 1-6 carbon atoms; —$OR^a$ groups; —$C(O)OR^a$ groups; —$OC(O)R^a$ groups; and —$C(O)R^a$ groups.

9. The composition of claim 1, wherein said non-coordinating monovalent anion is selected from halides, $SO_3CF_3^-$, $PF_6^-$, tosylate, $SbF_6^-$, borate anions, $AsF_6^-$, $ClO_4^-$, and carborane anions.

10. The composition of claim 1, wherein said rhenium(I) complex is dispersed in a pharmaceutically acceptable carrier.

11. A method for treating a condition in which inducing ER stress is beneficial, the method comprising administering to said subject a pharmaceutically effective amount of a composition of claim 1.

12. The method of claim 11, wherein said condition is a cancer.

13. The method of claim 12, wherein said cancer is a platinum-resistant cancer.

14. The method of claim 12, wherein said cancer is selected from ovarian cancer, cervical cancer, testicular cancer, prostate cancer, breast cancer, lung cancer, mesothelioma, squamous cell cancer, bladder cancer, lymphatic cancer, esophageal cancer, stomach cancer, gastrointestinal cancer, head-and-neck cancer, skin cancer, and pancreatic cancer.

15. The method of claim 11, wherein

has the following structure:

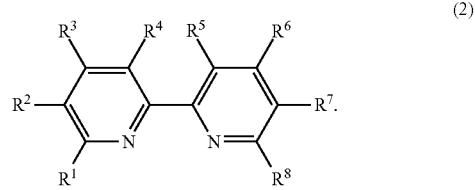

(2)

16. The method of claim 15, wherein at least $R^3$ and $R^6$ and/or $R^1$ and $R^8$ are not hydrogen atoms.

17. The method of claim 15, wherein at least two of $R^1$, $R^2$, $R^3$, $R^4$, $R^5$, $R^6$, $R^7$, and $R^8$ are independently selected from the group consisting of hydrocarbon groups (R') containing 1-6 carbon atoms; —$OR^a$ groups; —$C(O)OR^a$ groups; —$OC(O)R^a$ groups; and —$C(O)R^a$ groups.

18. The method of claim 15, wherein at least one of $R^1$, $R^2$, $R^3$, and $R^4$ and at least one of $R^5$, $R^6$, $R^7$, and $R^8$ are each independently selected from the group consisting of hydrocarbon groups (R') containing 1-6 carbon atoms; —$OR^a$ groups; —$C(O)OR^a$ groups; —$OC(O)R^a$ groups; and —$C(O)R^a$ groups.

19. The method of claim 11, wherein

has the following structure:

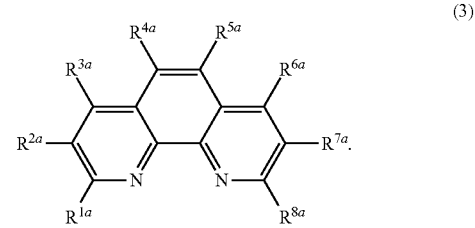

(3)

20. The method of claim 19, wherein at least $R^{1a}$ and $R^{8a}$ and/or $R^{3a}$ and $R^{6a}$ are not hydrogen atoms.

21. The method of claim 19, wherein at least one of $R^{1a}$, $R^{2a}$, $R^{3a}$, and $R^{4a}$ and at least one of $R^{5a}$, $R^{6a}$, $R^{7a}$, and $R^{8a}$ are each independently selected from the group consisting of hydrocarbon groups (R') containing 1-6 carbon atoms; —OR$^a$ groups; —C(O)OR$^a$ groups; —OC(O)R$^a$ groups; and —C(O)R$^a$ groups.

22. The method of claim 11, wherein said non-coordinating monovalent anion is selected from $SO_3CF_3^-$, $PF_6^-$, tosylate, $SbF_6^-$, borate anions, $AsF_6^-$, $ClO_4^-$, and carborane anions.

\* \* \* \* \*

UNITED STATES PATENT AND TRADEMARK OFFICE
CERTIFICATE OF CORRECTION

PATENT NO. : 11,884,685 B2  
APPLICATION NO. : 17/267687  
DATED : January 30, 2024  
INVENTOR(S) : Arthur Paden King et al.

Page 1 of 1

It is certified that error appears in the above-identified patent and that said Letters Patent is hereby corrected as shown below:

In the Specification

Column 1, Lines 15-16, delete:
"Department of Defense Ovarian Cancer Research Program"
And insert:
--U.S. Army Medical Research and Materiel Command--

Signed and Sealed this
Sixteenth Day of July, 2024

Katherine Kelly Vidal
*Director of the United States Patent and Trademark Office*